US008569466B2

(12) United States Patent
Ekwuribe

(10) Patent No.: US 8,569,466 B2
(45) Date of Patent: Oct. 29, 2013

(54) AROMATIC CARBOXYLIC ACID DERIVATIVES FOR TREATMENT AND PROPHYLAXIS OF GASTROINTESTINAL DISEASES INCLUDING COLON CANCERS

(76) Inventor: Nnochiri Ekwuribe, Cary, NC (US)

( * ) Notice: Subject to any disclaimer, the term of this patent is extended or adjusted under 35 U.S.C. 154(b) by 0 days.

(21) Appl. No.: 13/063,445

(22) PCT Filed: Sep. 10, 2009

(86) PCT No.: PCT/US2009/056515
§ 371 (c)(1),
(2), (4) Date: Sep. 12, 2011

(87) PCT Pub. No.: WO2010/030781
PCT Pub. Date: Mar. 18, 2010

(65) Prior Publication Data

US 2011/0319267 A1 Dec. 29, 2011

Related U.S. Application Data

(60) Provisional application No. 61/095,668, filed on Sep. 10, 2008.

(51) Int. Cl.
*C07C 309/24* (2006.01)
*C07C 245/06* (2006.01)
*C07C 245/08* (2006.01)
*A61K 31/185* (2006.01)
*A61K 31/353* (2006.01)
*A61K 31/655* (2006.01)

(52) U.S. Cl.
USPC ............ 534/660; 534/674; 534/847; 562/44; 514/562; 514/576

(58) Field of Classification Search
USPC .................................... 534/660, 674; 562/44
See application file for complete search history.

(56) References Cited

PUBLICATIONS

Schafer et al. Drug Discovery Today, 2008, 13 (21/22), 913-916.*
See Horig et al. Joumal of Translational Medicine 2004, 2(44), p. 1-8.*

* cited by examiner

*Primary Examiner* — Yong Chu
(74) *Attorney, Agent, or Firm* — Hultquist, PLLC; David Bradin

(57) ABSTRACT

Prodrug compounds which metabolize into 5-ASA or analogs thereof, and taurine or analogs thereof, in the colon site are disclosed. Pharmaceutical compositions including the compounds, and methods of treatment using the compounds, are also disclosed. Such compounds have utility for treating or preventing gastrointestinal disorders, including colon cancer, ulcerative colitis and Crohn's disease.

4 Claims, No Drawings

AROMATIC CARBOXYLIC ACID DERIVATIVES FOR TREATMENT AND PROPHYLAXIS OF GASTROINTESTINAL DISEASES INCLUDING COLON CANCERS

CROSS-REFERENCE TO RELATED APPLICATIONS

This application is a U.S. national phase application under the provisions of 35 U.S.C. §371 of International Patent Application No. PCT/US09/56515 filed Sep. 10, 2009, which in turn claims priority of U.S. Patent Application No. 61/095,668 filed Sep. 10, 2008. The disclosures of such international patent application and US priority patent application are hereby incorporated herein by reference in their respective entireties, for all purposes.

This application claims priority to U.S. Provisional Application No. 61/095,668, the contents of which are hereby incorporated by reference for all purposes.

FIELD OF THE INVENTION

The present invention relates to aromatic carboxylic acid derivatives for treatment and prophylaxis of gastrointestinal diseases including ulcerative colitis and colon cancer, as well as to therapeutic compositions comprising such derivatives, and methods of treatment and prophylaxis of gastrointestinal diseases using such derivatives and corresponding compositions.

DESCRIPTION OF THE RELATED ART

Inflammatory bowel diseases include ulcerative colitis (UC) and Crohn's disease. Both UC and Crohn's disease are characterized by abdominal pain, bloody diarrhea, and bowel wall inflammation. Approximately 1 million Americans suffer with UC or Crohn's disease. In Western Europe and the United States the prevalence of UC is 70 to 150 per 100,000 while the prevalence of Crohn's disease is 4- to 100 per 100,000. Males and females are equally affected. Overall, the incidence of UC appears to be stabilizing, but the incidence of Crohn's disease is increasing, especially among young people.

Although the cause of inflammatory bowel disease is unknown, recent experimental and clinical studies suggest that the initiation and pathogenesis of Crohn's disease and UC are multifactorial involving interactions among genetic, environmental, and immune factors. Recently IBD has been attributed to abnormal responses to environmental triggers in genetically susceptible individuals (1-3) Available data suggest that chronic gut inflammation may result from a dysfunctional immune response to components of normal gut flora. Although no specific bacteria have been implicated in the development of IBD in humans, in genetic models of IBD in mice and rats, specific bacteria have been shown to precipitate disease (4, 5) In addition, environmental factors other than microbes play a role in the pathogenesis of IBD as exemplified by the observation that smoking improves UC but worsens Crohn's disease (6).

There are no curative medical therapies for inflammatory bowel diseases; and even surgical resection of Crohn's disease is not a definitive cure, since the majority of patients have recurrent disease. Current treatments for inflammatory bowel disease fall into six classes: 1) corticosteroids, 2) aminosalicylates, 3) immunosuppressants, 4) antibiotics, 5) biologicals, and 6) probiotics (7). Although corticosteroids are effective short-term therapy long-term use is fraught with severe complications. Aminosalicylate drugs such as sulfasalazine or mesalamine (5-ASA) are the mainstay of treatment for mild and moderate disease. Immunosuppressant agents such as azathioprine and 6-mercaptpurine are used as steroid sparing agents but have a variety of adverse side effects, often precluding use in many patients. The benefit of antibiotic therapy has not been demonstrated in the overall management of this disease process but may be beneficial in patients with Crohn's disease. Antibiotics are not effective in ulcerative colitis. The importance of certain pro-inflammatory cytokines as critical mediators of gut inflammation was established by a recent series of clinical studies demonstrating that immunoneutralization of tumor necrosis factor-α (TNF-α) remarkably attenuated inflammation and tissue injury observed in Crohn's disease (8). Finally, probiotics have only recently come to light as potential therapies with the recognition that certain bacteria may predispose to IBD.

Ulcerative colitis, responds to therapy, and has a natural history that suggests that it is a disease spectrum. What is studied as a single disease may, in fact, be a blend of several conditions whose final common denominator is diffuse inflammation of the colon associated with distortion of crypts on microscopic examination. A particular subset of ulcerative colitis patients may respond more favorable to therapy at a given stage of disease than at another stage. The host, the luminal environment, the mucosal border, and the immune system and vascular endothelium participate in the pathogenesis and healing of disease. Therapy that approaches ulcerative colitis with these distinct participants in mind may yield more success than outcomes obtained in the past two decades.

Colon cancer and gastrointestinal diseases, such as ulcerative colitis and Crohn's disease, represent a major health concern. Colon cancer is currently one of the top five causes of death for both men and women in the United States. Surgical intervention for colon cancer has associated poor survival statistics. Accordingly, there is a compelling need for new therapeutic agents that can be readily administered, such as by oral administration, to combat such gastrointestinal disease states.

5-Aminosalicylic acid and other 5-aminosalicylates are the most common anti-inflammatory drugs for treating ulcerative colitis *"UC") and Crohn's disease. These compounds are typically administered in the form of azo prodrugs, which are activated by colonic bacterial enzymes to release 5-aminosalicylic acid as an anti-inflammatory agent. Representative 5-amino salicylic acid based drugs include Mesalamine (Asacol® and Pentasa®), and analogs in which the azo linkage breaks down to release another compound in addition to 5-aminosalicylic acid, for example, Sulfasalazine (Azafuldine®), Olsalazine (Dipentum®), and Balsalazide (Colazal®). The formula for Balsalazide is shown below:

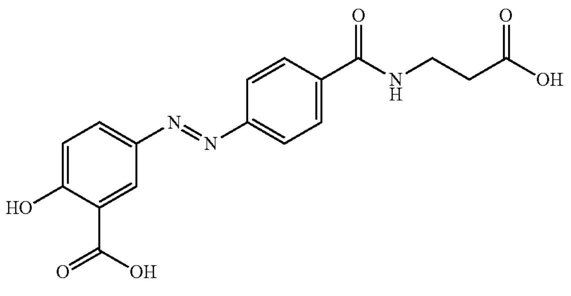 [SMILES: O=C(O)CCNC(=O)c1ccc(/N=N/c2ccc(O)c(C(=O)O)c2)cc1]

Another compound similar to balsalazide, but with a sulfonic acid rather than a carboxylic acid off of the —CO($NHCH_2CH_2$—) side chain, is disclosed in U.S. Pat. No. 4,412,992.

In addition to 5-aminosalicylic acid, there are other compounds known to have a positive effect when administered to the colon site. One example is taurine, which is known for its immunomodulatory and anti-inflammatory properties when administered to the colon. Zhao et al., "Attenuation by dietary taurine of dextran sulfate sodium-induced colitis in mice and of THP-1-induced damage to intestinal Caco-2 cell monolayers," Amino Acids Jul. 6 (2007), the contents of which are hereby incorporated by reference.

It is believed that, to date, there have been no pro-drug forms of taurine identified as delivering taurine to the colon.

It would be advantageous to provide additional therapeutic agents, and methods for using such agents to treating and/or prevent gastrointestinal diseases, including colon cancers, ulcerative colitis and Crohn's disease. The present invention provides such agents and methods.

SUMMARY OF THE INVENTION

The present invention is directed to compounds, pharmaceutical compositions including the compounds, and methods for treating and preventing gastrointestinal disorders. Representative disorders that can be treated include ulcerative colitis, Crohn's disease, and colon cancer.

In one embodiment, the compounds are conjugates of aromatic carboxylic acids and immunomodulators, anti-inflammatory agents, or anti-cancer drugs. In one aspect of this embodiment, the compounds include an amine or hydroxy group.

In one embodiment, the conjugates are prodrugs of active compounds, and are prepared by forming one or more azo, amide, urea, thiourea, carbamate, thiocarbamate, or imine linkages between aromatic carboxylic acids and various amine-containing or hydroxy-containing compounds.

Where the linkages comprise azo linkages, bacterial azoreductase enzymes in the colon can cleave the linkage and free active compounds. Where the linkages comprise amide linkages, amidase enzymes in the colon can cleave the linkages and free active compounds. Where the linkages comprise urea or thiourea linkages, bacterial ureas enzymes in the colon can cleave the linkages and free active compounds.

Ulcerative colitis and Crohn's disease are inflammatory diseases, and are frequently controlled with immuno-modulating agents. Accordingly, in some aspects of the invention, the conjugates described herein are prodrugs that treat both inflammation and modulate the immune system. Representative immunomodulating agents include taurine and taurine analogs, such as analogs where the —$SO_3H$ group is replaced with a sulfonamide group (—$SO_2NHR^6$, where $R^6$ is H or $C_{1-8}$ alkyl) or a —$SO_2N_3$ group. Representative anti-inflammatory agents include 5-amino-salicyclic acid and apocrit.

Prodrugs that combine immunoregulatory compounds with 5-aminosalicylic acid via biodegradable linkages can provide an effective treatment of gastrointestinal disorders, such as UC and Crohn's disease. Upon colonic enzyme activation of the prodrug, 5-aminosalicylic acid, as well as the immunoregulatory component, will be released. Because of the immunoregulatory component of the drug, it is expected to treat the disease while modulating the immune system, which provides advantages over other 5-aminosalicylic acid-containing prodrugs currently in the market.

In one embodiment, the compounds include, as metabolites, one of more of the following:

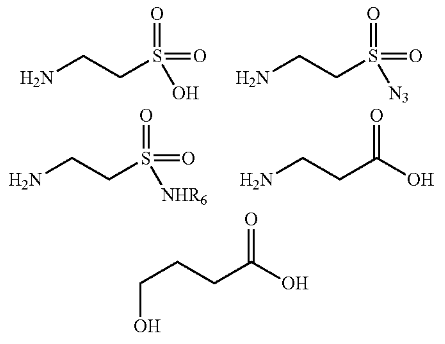

as well as one of the following:

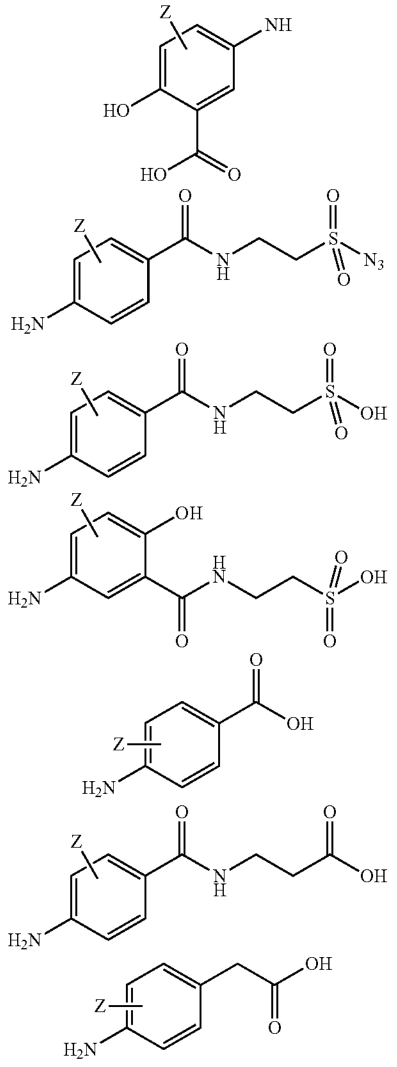

In this embodiment, the metabolites are formed when a degradable linkage is cleaved in vivo to yield the above-listed metabolites. In describing the chemistry, it is important to recognize that the above-listed metabolites are formed from compounds that are not necessarily identical to the metabolites. That is, an aromatic amine-containing compound (a first putative metabolite) can be reacted with sodium nitrite to form a diazonium salt, which then reacts with a second putative metabolite to form an azo linkage. The second putative metabolite did not start with an amine group, and the amine group only forms when the diazo group linking the first and second putative metabolites biodegrades in the colon.

In another embodiment, an isocyanate group (—N═C═O) can be present instead of an amine group when the prodrug is formed, and when it reacts with an amine group on another of the metabolites, it forms a urea linkage (—N—(C═O)—N—). A thioisocyanate group (—N═C═S) can be used to form a thiourea. If the other putative metabolite includes a hydroxy group, an isocyanate can react with the hydroxy group to form a carbamate linkage (—N—(C═O)—O—), and an isothiocyanate can react with the hydroxy group to form a thiocarbamate linkage (—N—(C═S)—O—). The urea, carbamate, thiourea, and thiocarbamate linkages can also be prepared in a step-wise fashion, using a compound such as phosgene, diphosgene, triphosgene, thio versions of these compounds (I.e., ClC(═S)Cl), and compounds such as ClC(═O)O-alkyl, where alkyl is typically methyl or ethyl.

Carboxylic acid moieties on one putative metabolite can react with amine moieties on another putative metabolite to form amide linkages. A carbonyl moiety on one putative metabolite can react with an amine moiety on another putative metabolite to form an imine linkage.

In another embodiment, the compounds are formed from epigenin analogs and one or more of the compounds listed above. Compounds with amine groups, such as 5-ASA, can be reacted with the epigenin analogs to form imine linkages. Alternatively, where the desired metabolite has an amine group, a carbamate linkage can be formed between the putative amine group (i.e., the amine group to be formed in vivo) and a hydroxy group on the epigenin analog, by reacting an isocyanate group on the putative metabolite with one or both of the hydroxy groups on the epigenin analog. To form a thiocarbamate, an isothiocyanate group can be used.

Representative chemistry is shown below:

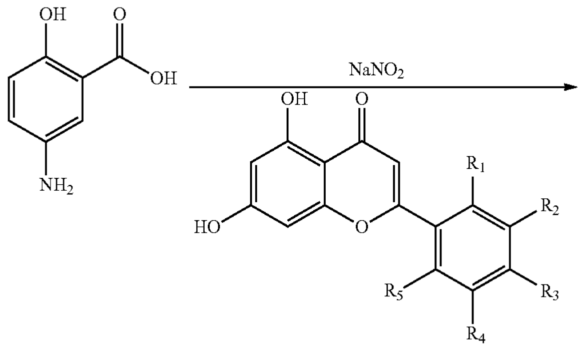

-continued

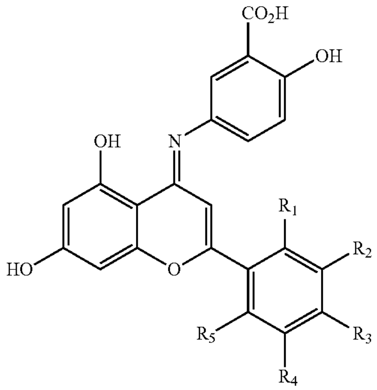

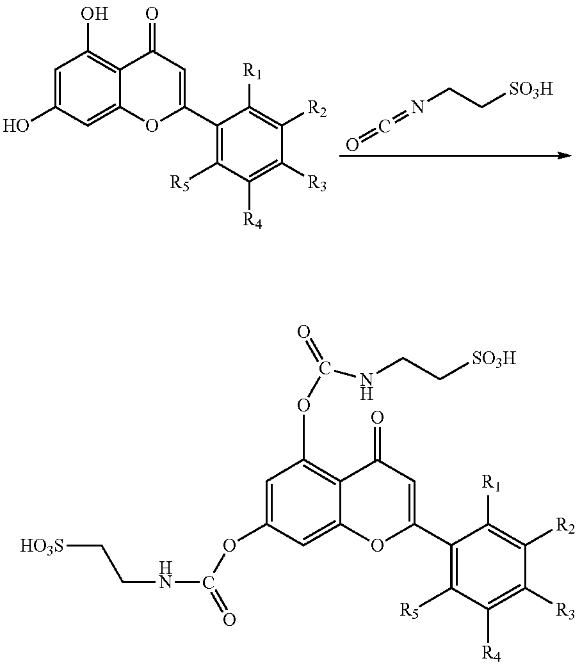

In one aspect, the present invention relates to a compound selected from among compounds of the formulae (I)-(III):

(I)

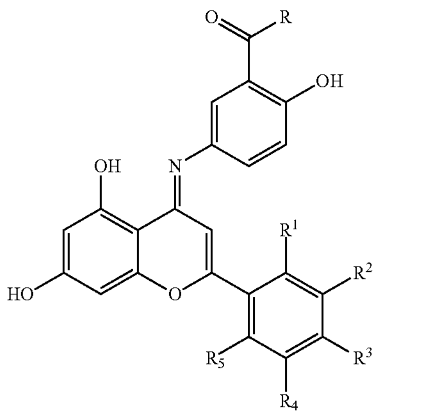

(II)

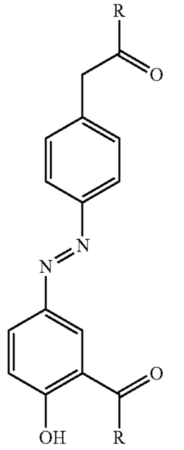

(III)

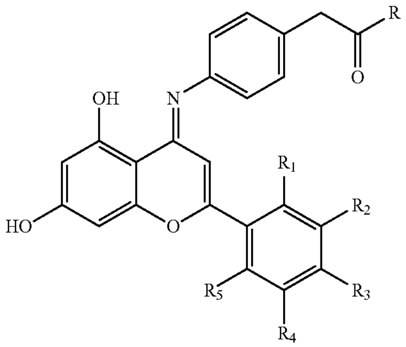

wherein:

each R is independently selected from among —OH, —$HNCH_2CH_2SO_3H$, —$HNCH_2CH_2SO_2N_3$, —$HNCH_2CH_2SO_2NHR^6$, —$HNCH_2CO_2H$ and —$HNCH(CO_2H)CH_2COOH$; and each of $R^1$, $R^2$, $R^3$, $R^4$ and $R^5$ is independently selected from among H and OH; and pharmaceutically acceptable salts and esters thereof.

In another aspect, the invention relates to a compound of the formula:

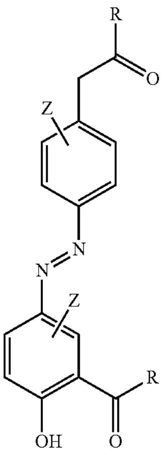

wherein the carboxy R group on the benzyl moiety at the upper portion of the molecule in the formula shown is hydroxyl, and the carboxy R group on the phenyl moiety at the lower portion of the molecule in the formula shown is $HNCH_2CH_2SO_3H$. The substituent Z can be any substituent that does not interfere with the coupling chemistry, or which can be protected during the coupling chemistry, and deprotected afterwards to yield the desired substituent. Representative substituents are defined elsewhere herein.

A further aspect of the invention relates to a compound selected from among:

(IV)

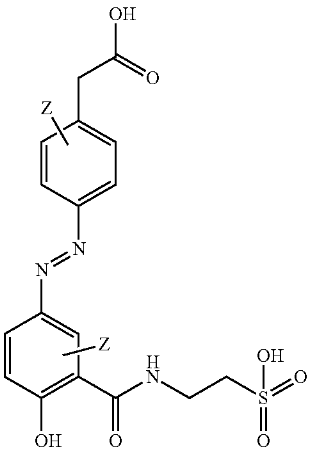

(V)

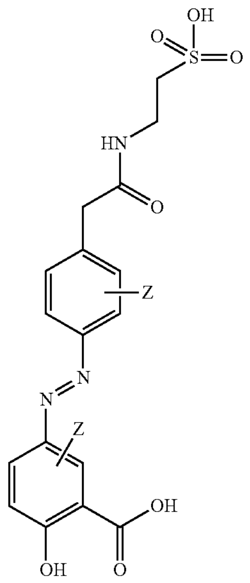

-continued
(VI)
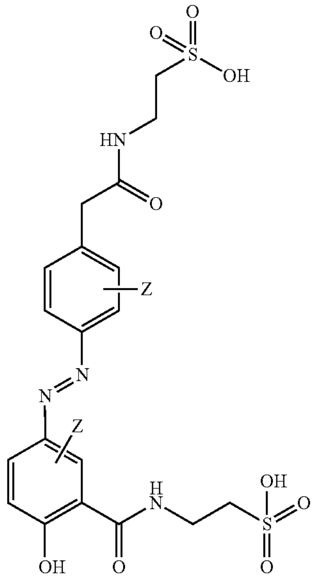
(VII)
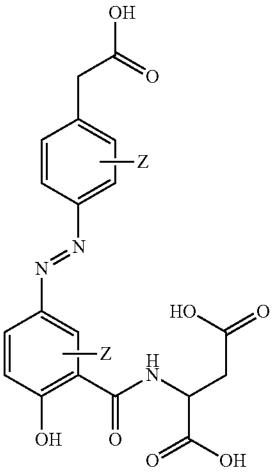
(VIII)
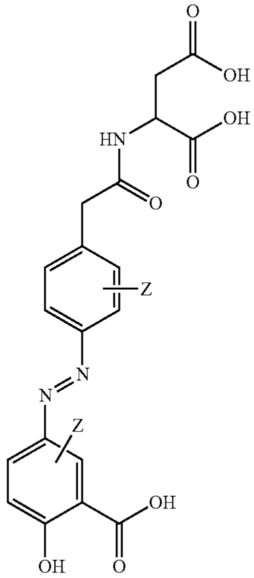
-continued
(IX)
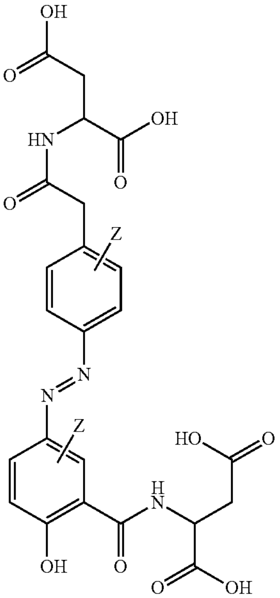
(X)
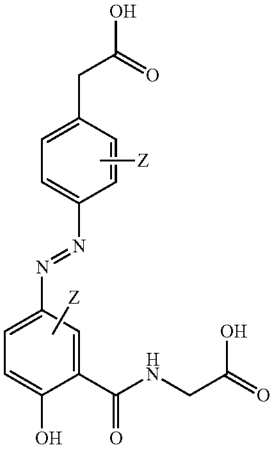
(XI)
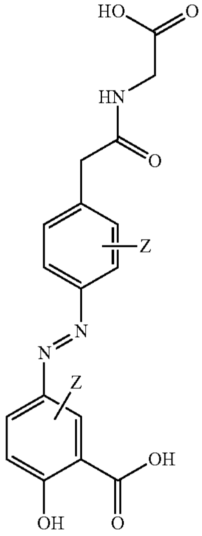

-continued (XII)

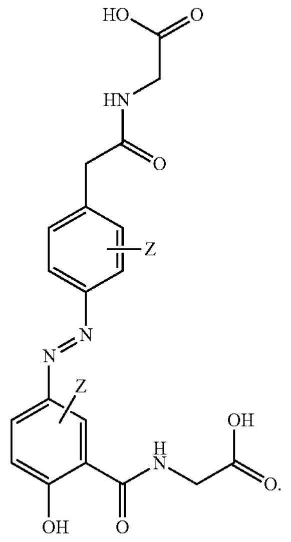

The invention in yet another aspect relates to a method for treatment or prophylaxis of a disorder of the gastrointestinal tract in a subject in need of such treatment, said method comprising administering to the subject a pharmaceutical composition comprising a compound of the invention.

A further aspect of the invention relates to such a method of treatment or prophylaxis, wherein said disorder includes one or more of colon cancer, mucositis, Crohn's disease, esophagitis, conditions resulting from chemical injury, gastroesophageal reflux disease, bile acid reflux, Barrett's esophogas, esophageal stricture, gastritis, peptic ulcer disease, precancerous lesions of the stomach, non-ulcer dyspepsia, celiac disease, bacterial overgrowth, fissures of the intestine, ulcerative colitis, irritable bowel syndrome, inflammatory bowel disorder, infectious colitis, radiation-induced colitis, colitis in an immunocompromised host, precancerous conditions of the colon, proctitis, inflammation associated with hemorrhoids, proctalgia fugax, rectal fissures, cholangitis, sclerosing cholangitis, primary bilary cirrhosis, cholecystitis and intestinal abscess.

In a further aspect, the invention relates to a therapeutic composition comprising a dose form including one of more of compounds (XVIII)-(XV):

(XIII)

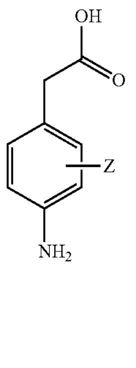

-continued (XIV)

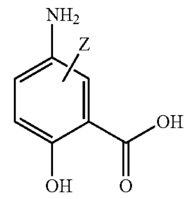

(XV)

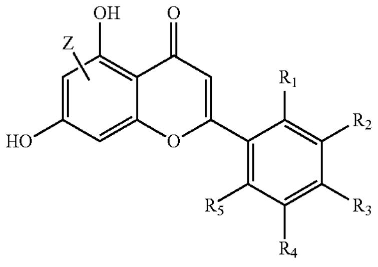

wherein each of $R^1$, $R^2$, $R^3$, $R^4$ and $R^5$ is independently selected from among H and OH, or prodrug versions of these compounds, which form these compounds upon exposure to bacterial enzymes in the colon site.

Additional compounds of the invention include the following compounds with anticipated metabolites that include 5-ASA and taurine:

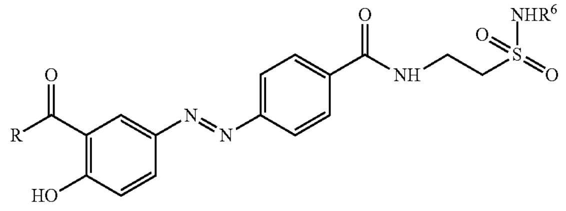

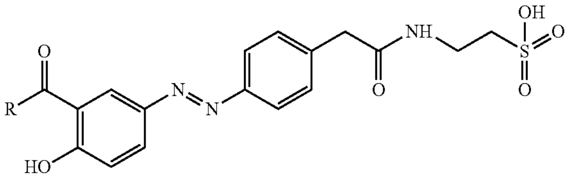

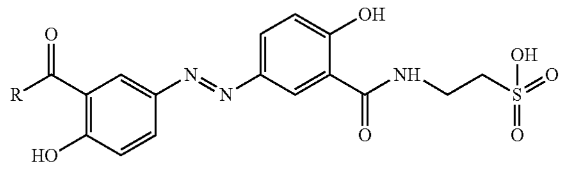

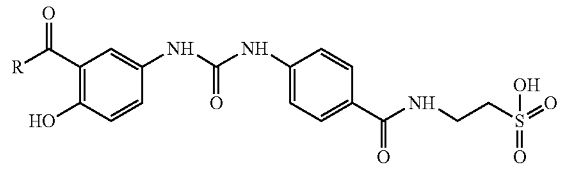

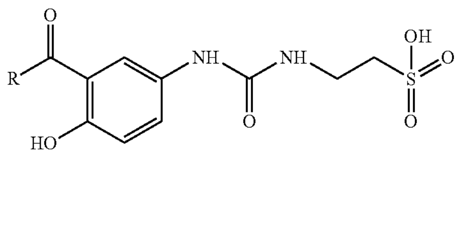

-continued

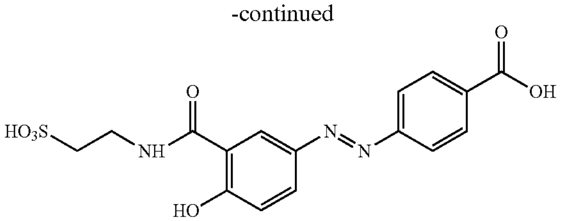

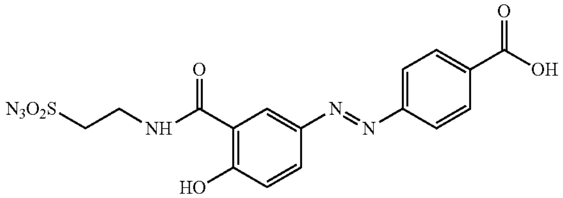

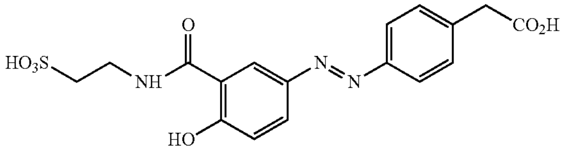

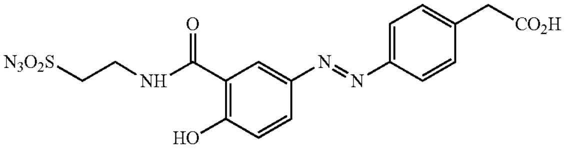

wherein R is selected from the group consisting of —OH, $—HNCH_2CH_2SO_3H$, $—HNCH_2CH_2SO_2N_3$, $—HNCH_2CH_2SO_2NHR^6$, $—HNCH_2CO_2H$ and $—HNCH(CO_2H)CH_2COOH$. In one embodiment, each R is —OH.

Additional compounds include those where the urea is replaced with a thiourea, where the sulfonic acid group is replaced with an $—SO_2N_3$ or sulfonamide group, and compounds including both of these replacements. Further additional compounds include compounds where the amine group on taurine (and analogs of taurine in which the sulfonic acid group is replaced with an $—SO_2N_3$ or sulfonamide group) is coupled to 5-ASA via an amide or thioamide linkage.

The invention in another aspect relates to a method of treatment for prophylaxis of a gastrointestinal disorder in the subject in need thereof, said method comprising delivering to or generating at a gastrointestinal locus one of more of compounds (XVIII)-(XV):

(XIII)

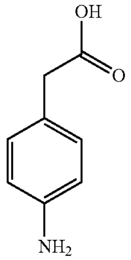

(XIV)

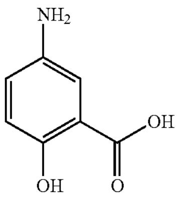

-continued (XV)

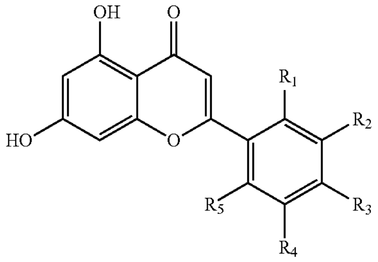

wherein each of $R^1$, $R^2$, $R^3$, $R^4$ and $R^5$ is independently selected from among H and OH, and/or a compound of the following formulas:

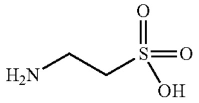

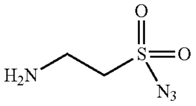

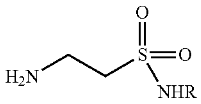

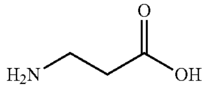

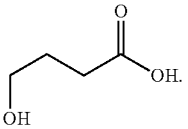

wherein the compounds are administered in the form of prodrugs, and metabolize in vivo to form the active compounds.

A further aspect of the invention relates to a method of synthesizing a compound of Formula (I), said method comprising the following reaction scheme:

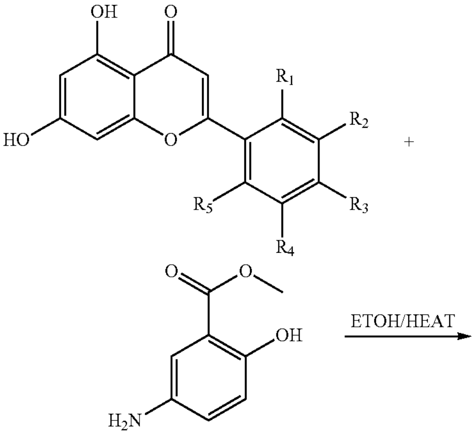

-continued

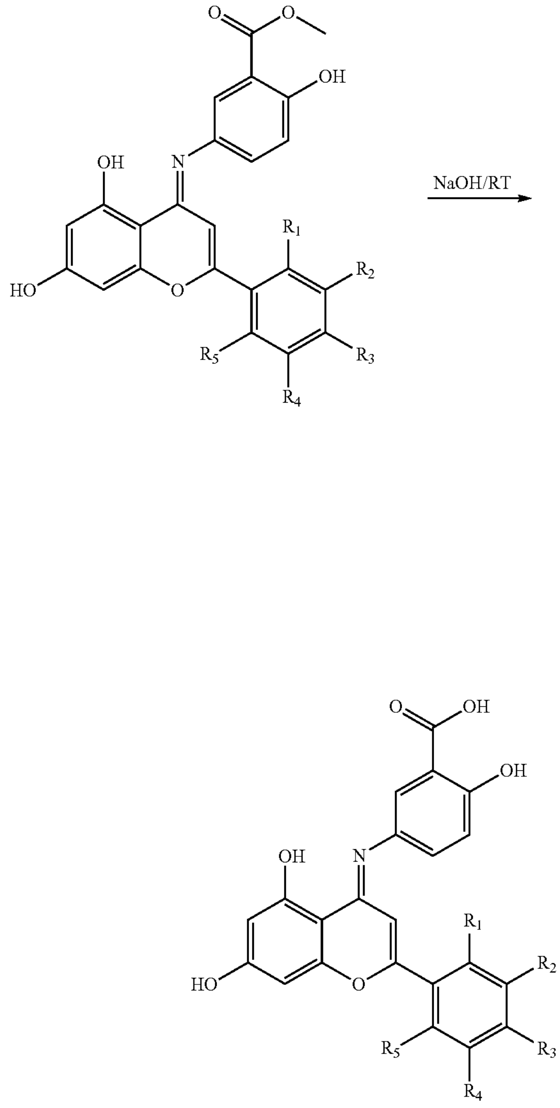

wherein each of $R^1$, $R^2$, $R^3$, $R^4$ and $R^5$ is independently selected from among H and OH.

Another aspect of the invention relates to a method of synthesizing a compound of Formula (II), said method comprising one of the following reaction schemes:

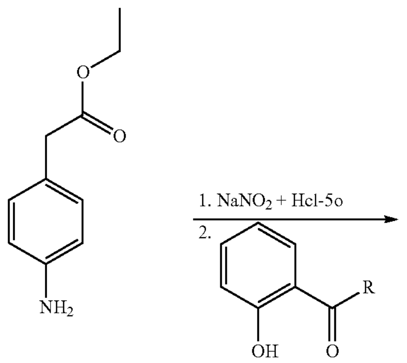

-continued

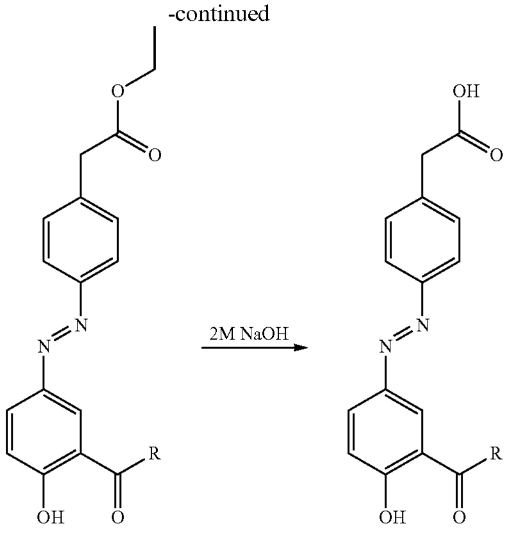

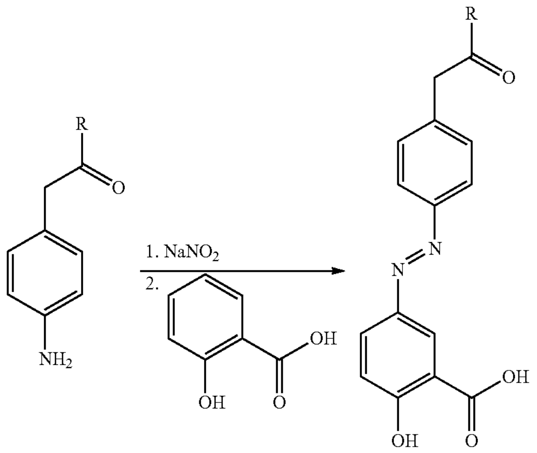

and

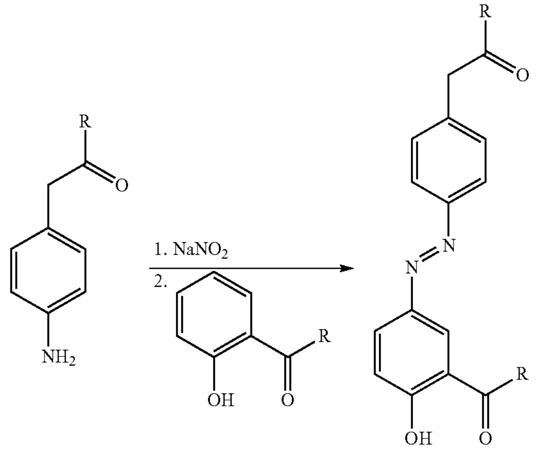

wherein each R is independently selected from among OH, $HNCH_2CH_2SO_3H$, $HNCH_2CO_2H$ and $HNCH(CO_2H)CH_2COOH$.

Yet another aspect of the invention relates to a method of synthesizing a compound of Formula (III), said method comprising the following reaction scheme:

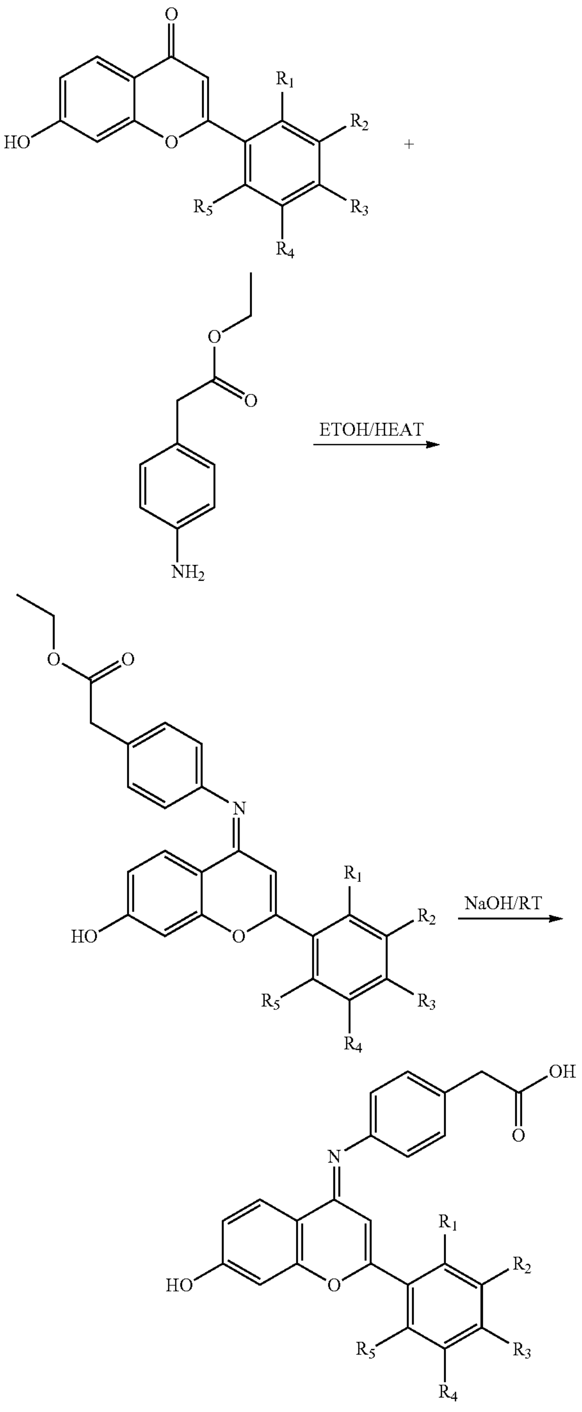

wherein each of $R^1$, $R^2$, $R^3$, $R^4$ and $R^5$ is independently selected from among H and OH.

Another aspect of the invention relates to a pharmaceutical composition, comprising a compound of the invention, and a co-active ingredient selected from among anti-inflammatory agents, immunomodulators, steroidal compounds and antibiotics.

These and other aspects, features and embodiments of the invention will be more fully apparent from the ensuing disclosure and appended claims.

DETAILED DESCRIPTION

Compounds, pharmaceutical compositions including the compounds, and methods of preparation and use thereof are disclosed.

The following definitions will be useful in understanding the metes and bounds of the invention as described herein.

As used herein, "alkyl" refers to straight chain or branched saturated hydrocarbon radicals including $C_1$-$C_8$, preferably $C_1$-$C_5$, such as methyl, ethyl, or isopropyl.

The term "substituted alkyl" refers to alkyl radicals further bearing one or more substituent groups such as hydroxy, alkoxy, aryloxy, mercapto, aryl, heterocyclo, halo, amino, carboxyl, carbamyl, cyano, and the like.

The term "alkenyl" refers to straight chain or branched hydrocarbon radicals including $C_1$-$C_8$, preferably $C_1$-$C_5$ and having at least one carbon-carbon double bond; "substituted alkenyl" refers to alkenyl radicals further bearing one or more substituent groups as defined above.

The term "cycloalkyl" refers to saturated or unsaturated, non-aromatic, cyclic ring-containing radicals containing three to eight carbon atoms, preferably three to six carbon atoms.

The term "substituted cycloalkyl" refers to cycloalkyl radicals further bearing one or more substituent groups as defined above.

The term "amino" refers to amine groups bearing zero, one, or two alkyl groups, and includes cyclic amines with ring sizes between three and eight carbons; "aryl" refers to aromatic radicals having six to ten carbon atoms.

The term "substituted aryl" refers to aryl radicals further bearing one or more substituent groups as defined above.

The term "alkylaryl" refers to alkyl-substituted aryl radicals, whereas "substituted alkylaryl" refers to alkylaryl radicals further bearing one or more substituent groups as defined above.

The term "arylalkyl" refers to aryl-substituted alkyl radicals, whereas "substituted arylalkyl" refers to arylalkyl radicals further bearing one or more substituent groups as defined above.

The term "heterocyclyl" refers to saturated or unsaturated cyclic radicals containing one or more heteroatoms (e.g., O, N, S) as part of the ring structure and having two to seven carbon atoms in the ring, whereas "substituted heterocyclyl" refers to heterocyclyl radicals further bearing one or more substituent groups as defined above.

The substituent Z can be any substituent that does not interfere with the coupling chemistry, or which can be protected during the coupling chemistry, and deprotected afterwards to yield the desired substituent. The protection and deprotection steps also apply to any —OH, $—NH_2$, $—CO_2H$, $—SO_3H$, and $SO_2NHR^6$ groups that need to be protected during the various coupling steps. Suitable protecting groups for these moieties are found, for example, in Greene and Wuts, Protective Groups in Organic Synthesis, Third Ed., Wiley Interscience, NY, N.Y. (1999).

Representative substituents, Z, include H, $C_{1-6}$ alkyl (including cycloalkyl), alkenyl, heterocyclyl, aryl, heteroaryl, halo (e.g., F, Cl, Br, or I), —OR', —NR'R", $—CF_3$, —CN, $—NO_2$, $—C_2R'$, —SR', $—N_3$, —C(═O)NR'R", —NR'C(═O)R", —C(═O)R', —C(═O)OR', —OC(═O)R', —OC(═O)NR'R", —NR'C(═O)O R", $—SO_2R'$, $—SO_2NR'R"$, and $—NR'SO_2R"$, where R' and R" are individually hydrogen, $C_{1-6}$ alkyl, cycloalkyl, heterocyclyl, aryl, or arylalkyl (such as benzyl).

I. Compounds

The compounds are aromatic carboxylic acid derivatives useful for treating and preventing gastrointestinal diseases including ulcerative colitis and colon cancer.

The aromatic carboxylic acid derivatives described herein can be orally administered to treat or prevent gastrointestinal diseases such as ulcerative colitis, Crohn's disease and colon cancer, and as a result of their structure traverse the upper gastrointestinal tract in an non-degraded state, and in such non-degraded state reach the colon, where the molecule is cleaved by colonic enzymes to form active metabolite species.

The present invention also contemplates in another aspect the delivery of active metabolites to the colon, by administration of the aromatic carboxylic acid derivatives of the invention and in vivo formation of the active metabolite species, by action of colonically active enzymes on the aromatic carboxylic acid derivatives, or by administration of the active metabolite species, in a dose form or formulation in which they are bioavailable at the colonic locus.

Additional compounds of the invention include the following compounds with anticipated metabolites that include 5-ASA and taurine:

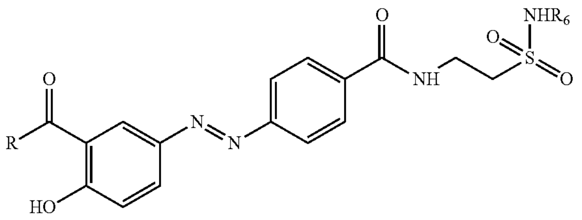

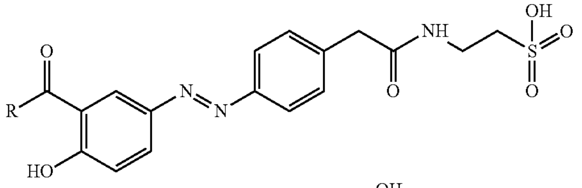

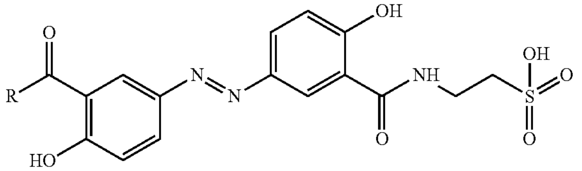

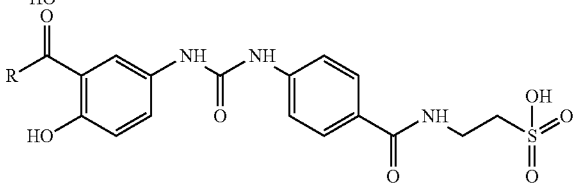

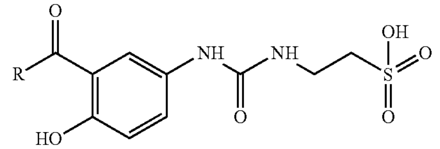

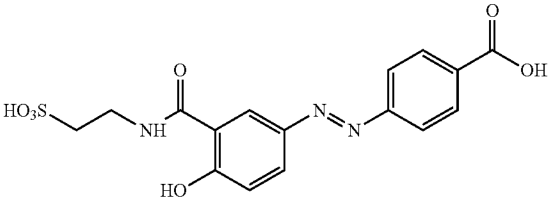

-continued

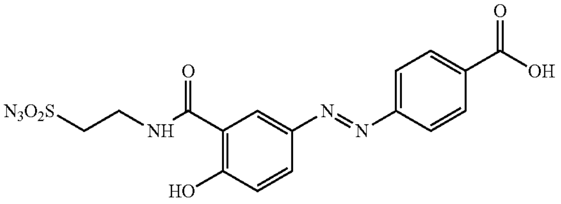

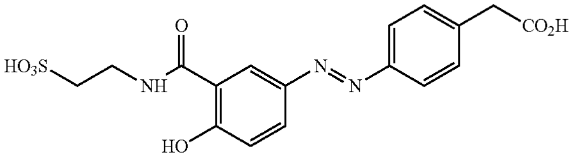

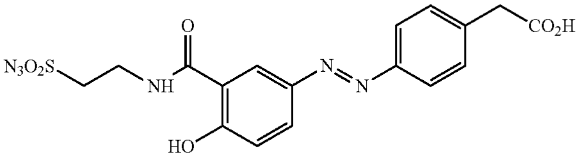

wherein R is selected from the group consisting of —OH, $-HNCH_2CH_2SO_3H$, $-HNCH_2CH_2SO_2N_3$, $-HNCH_2CH_2SO_2NHR^6$, $-HNCH_2CO_2H$ and $-HNCH(CO_2H)CH_2COOH$. In one embodiment, each R is —OH.

Additional compounds include those where the urea is replaced with a thiourea, where the sulfonic acid group is replaced with an $-SO_2N_3$ or sulfonamide group, and compounds including both of these replacements. Further additional compounds include compounds where the amine group on taurine (and analogs of taurine in which the sulfonic acid group is replaced with an $-SO_2N_3$ or sulfonamide group) is coupled to 5-ASA via an amide or thioamide linkage.

The invention in another aspect relates to a method of treatment for prophylaxis of a gastrointestinal disorder in the subject in need thereof, said method comprising delivering to or generating at a gastrointestinal locus one of more of compounds (XVIII)-(XV):

(XIII)

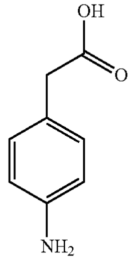

(XIV)

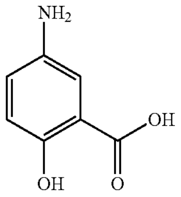

-continued (XV)

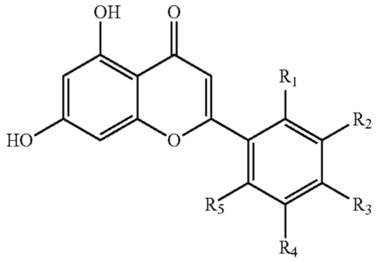

wherein each of $R^1$, $R^2$, $R^3$, $R^4$ and $R^5$ is independently selected from among H and OH, and/or a compound of the following formulas:

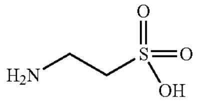

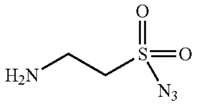

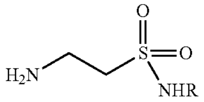

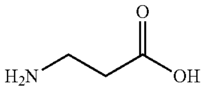

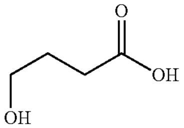

The aromatic carboxylic acid derivatives of the present invention include the compounds of the formulae (I)-(III):

(I)

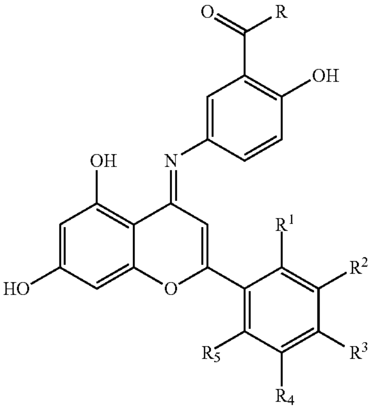

-continued (II)

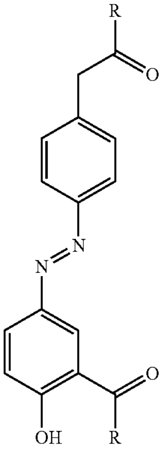

(III)

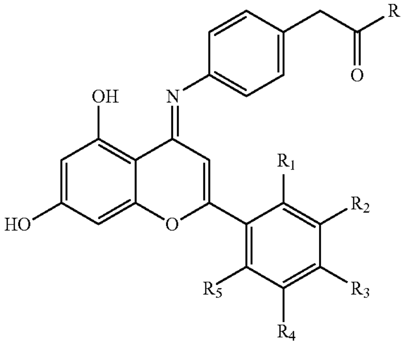

wherein:

each R is independently selected from the group consisting of —OH, $—HNCH_2CH_2SO_3H$, $—HNCH_2CH_2SO_2N_3$, $—HNCH_2CH_2SO_2NHR^6$, $—HNCH_2CO_2H$ and $—HNCH(CO_2H)CH_2COOH$;

each of $R^1$, $R^2$, $R^3$, $R^4$ and $R^5$ is independently selected from among H and OH; and $R^6$ is H or $C_{1-8}$ alkyl, and pharmaceutically acceptable salts and esters thereof.

Preferred aromatic carboxylic acid derivatives of the invention include the compound of Formula (II) above:

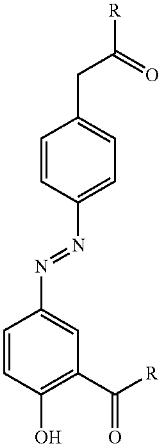

wherein each R is independently selected from among R is selected from the group consisting of —OH, —$HNCH_2CH_2SO_3H$, —$HNCH_2CH_2SO_2N_3$, —$HNCH_2CH_2SO_2NHR^6$, —$HNCH_2CO_2H$ and —$HNCH(CO_2H)CH_2COOH$, and $R^6$ is H or $C_{1-8}$ alkyl.

A particularly preferred compound of such type is:

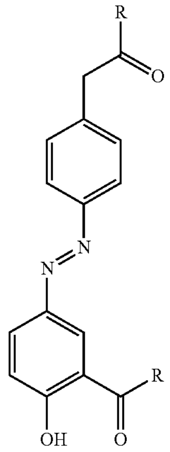

wherein the carboxy R group on the benzyl moiety at the upper portion of the molecule in the formula shown is hydroxyl, and the carboxy R group on the phenyl moiety at the lower portion of the molecule in the formula shown is $HNCH_2CH_2SO_3H$.

Specific compounds usefully employed to combat gastrointestinal disorders in the broad practice the present invention include the following:

(IV)

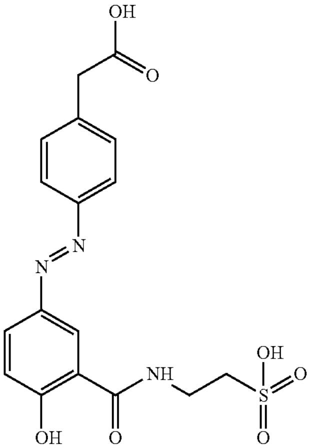

-continued (V)

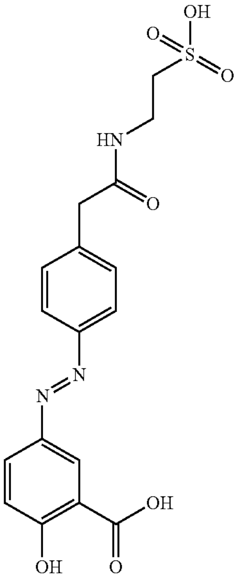

(VI)

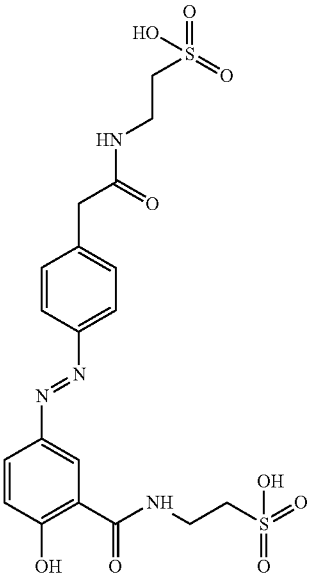

(VII)

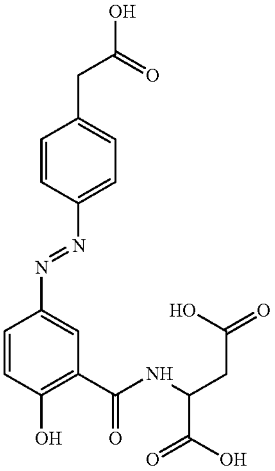

-continued (VIII)

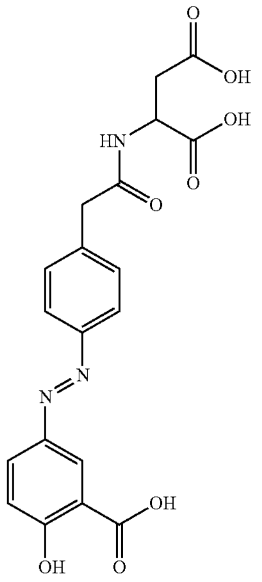

(IX)

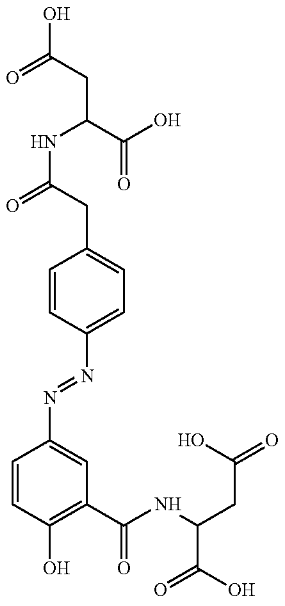

(X)

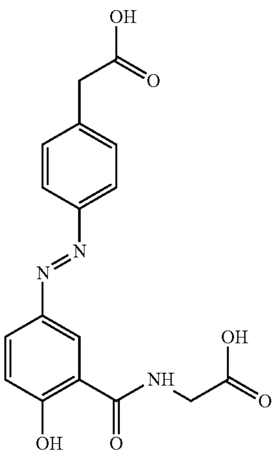

-continued (XI)

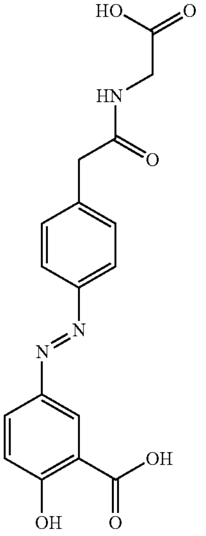

(XII)

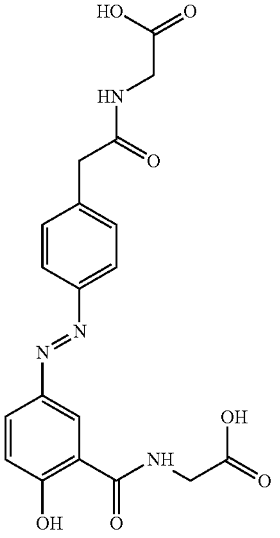

II. Methods of Preparing the Compounds

In one embodiment, the compounds can be prepared by reacting an appropriately functionalized amine-containing aromatic carboxylic acid, such as 5-amino salicyclic acid, with sodium nitrite to form a diazonium salt, then reacting the diazonium salt with an appropriately functionalized second aromatic compound to form an azo linkage between the two aromatic rings. The position of the azo linkage is largely determined by a) the position of the amine group on the amine-containing aromatic carboxylic acid, and b) the presence of substituent groups on the second aromatic ring, where electron withdrawing substituents tend to orient the linkage to the meta position, and electron donating substituents tend to orient the linkage to the orth- and para-positions. Those of skill in the art understand the likely orientation of the azo linkage based on the well-known orientation of the various functional groups in electrophilic aromatic substitution reactions, such as the reaction of a diazonium salt with an aromatic ring.

The azo linkage can be cleaved in the colon site by bacterial azo-reductase enzymes to form two amine-containing aromatic compounds.

In another embodiment, the compounds include a urea or thiourea linkage. These compounds can be prepared by reacting a compound with an isocyanate group with a second compound that includes an amine group to form a urea linkage. This embodiment is particularly useful for linking aromatic rings and non-aromatic compounds (for example, to form prodrug forms of non-aromatic immunomodulatory compounds). However, it can also be used to link two aromatic rings. The isocyanate and amine groups can be present on either of the two compounds to be linked, as such would form the same urea linkage. To form a thiourea, one of the compounds to be linked would include an isothiocyanate rather than an isocyanate group, and react with an amine group on the second molecule. If the immunomodulatory compound includes a hydroxy, rather than an amine group, a carbamate or thiocarbamate linkage can be formed.

The urea linkage can be cleaved in the colon site by bacterial urease enzymes to form two amine-containing aromatic compounds, or one amine-containing aromatic compound and one non-aromatic amine.

Useful prodrugs of the present invention can also be formed that include an amide linkage. This is particularly useful where one active compound has a carboxylic acid group, and another compound has an amine group.

Set out below is a synthetic transformation scheme (Scheme 1), in which the synthesis of aromatic carboxylic acid derivatives of the invention, and the resulting active moieties produced at the colonic locus by colonic enzymes on such derivatives, are formulaically specified.

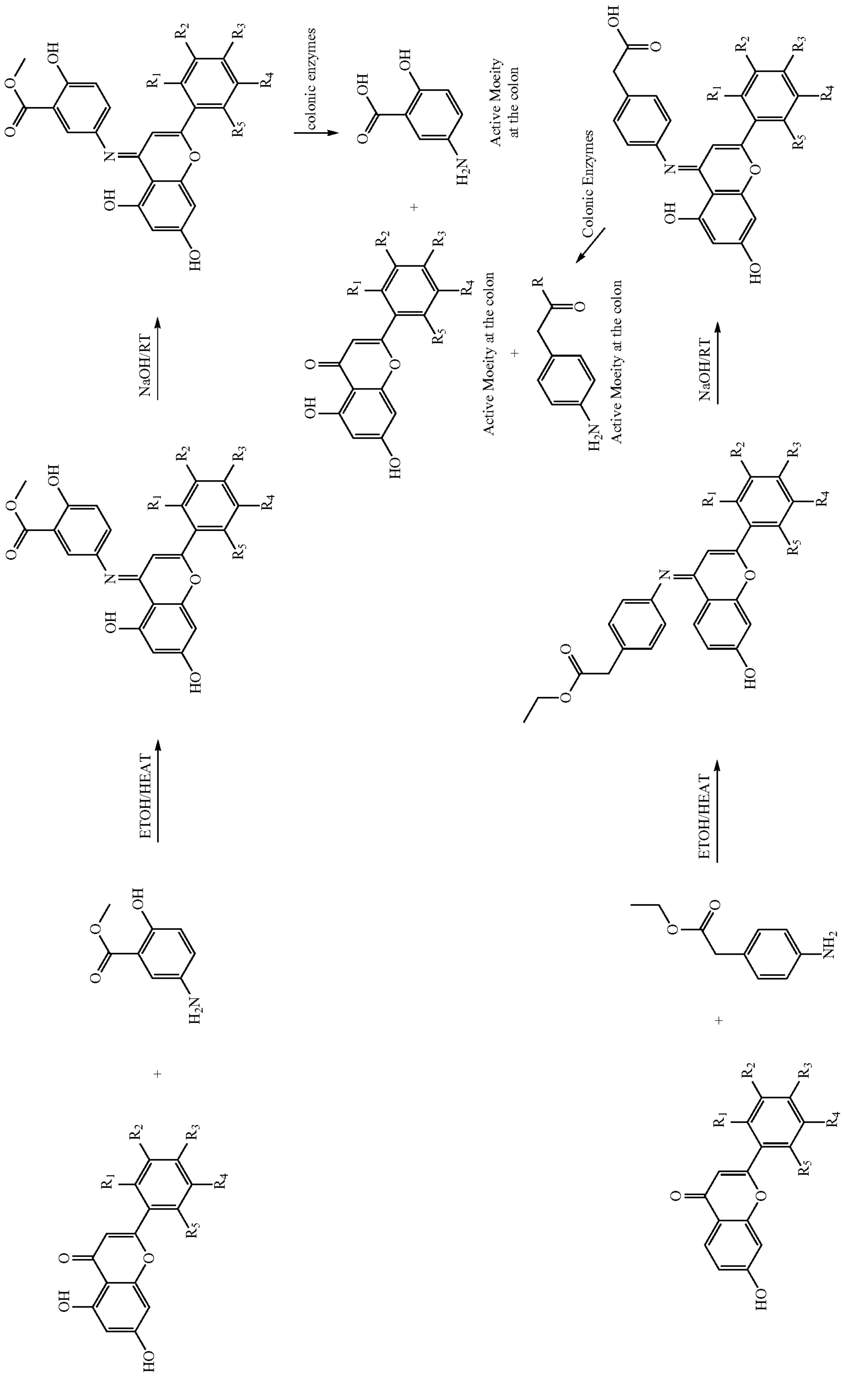
ETOH/HEAT
NaOH/RT
colonic enzymes
Active Moeity
at the colon
Active Moeity at the colon
Active Moeity at the colon
Colonic Enzymes
ETOH/HEAT
NaOH/RT wherein each of $R^1$, $R^2$, $R^3$, $R^4$ and $R^5$ is independently selected from among H and OH.

Set out below is another synthetic transformation scheme (Scheme 2), in which the synthesis of aromatic carboxylic acid derivatives of the invention, and the resulting active moieties produced at the colonic locus by colonic enzymes on such derivatives, are formulaically specified.

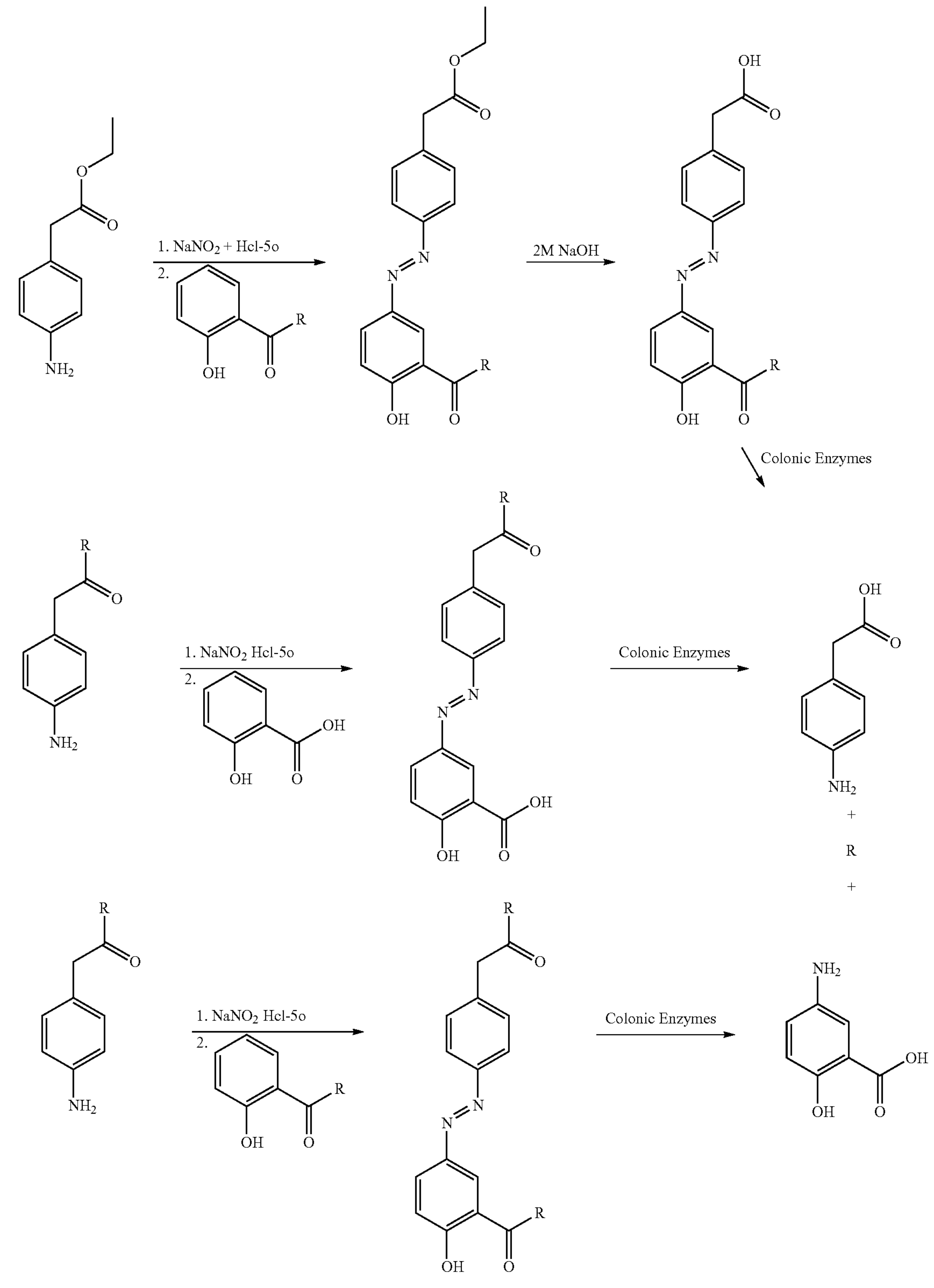

wherein R is selected from the group consisting of —OH, $—HNCH_2CH_2SO_3H$, $—HNCH_2CH_2SO_2N_3$, $—HNCH_2CH_2SO_2NHR^6$, $—HNCH_2CO_2H$ and $—HNCH(CO_2H)CH_2COOH$.
Reaction schemes for producing prodrug forms that include both taurine and 5-ASA as metabolites are provided below.
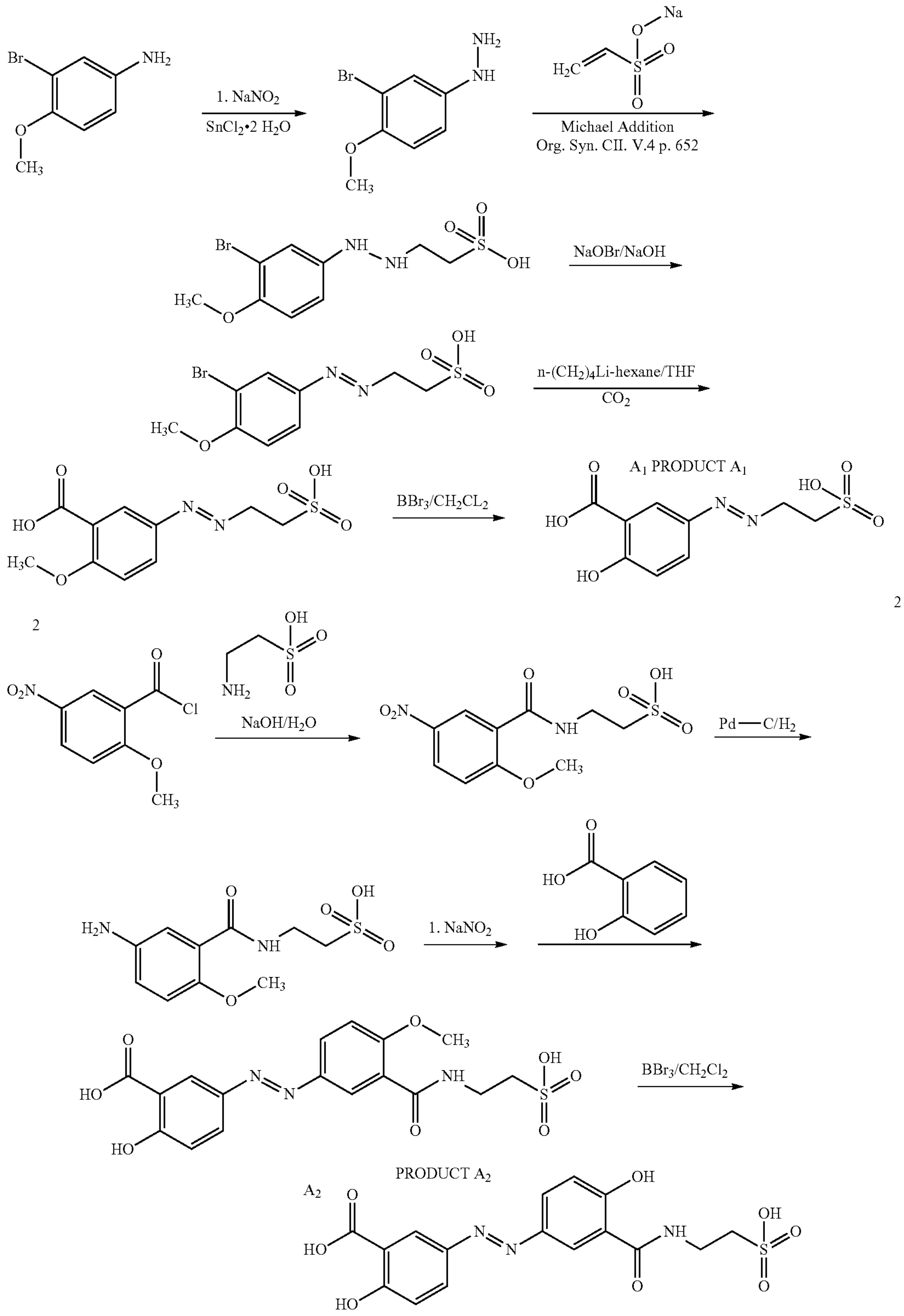

-continued
3
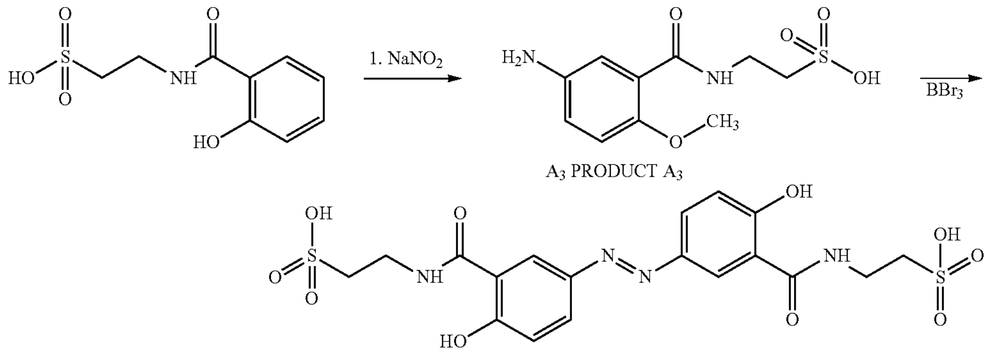
1
SYNTHESIS OF 5-ASA UREA COMPOUNDS
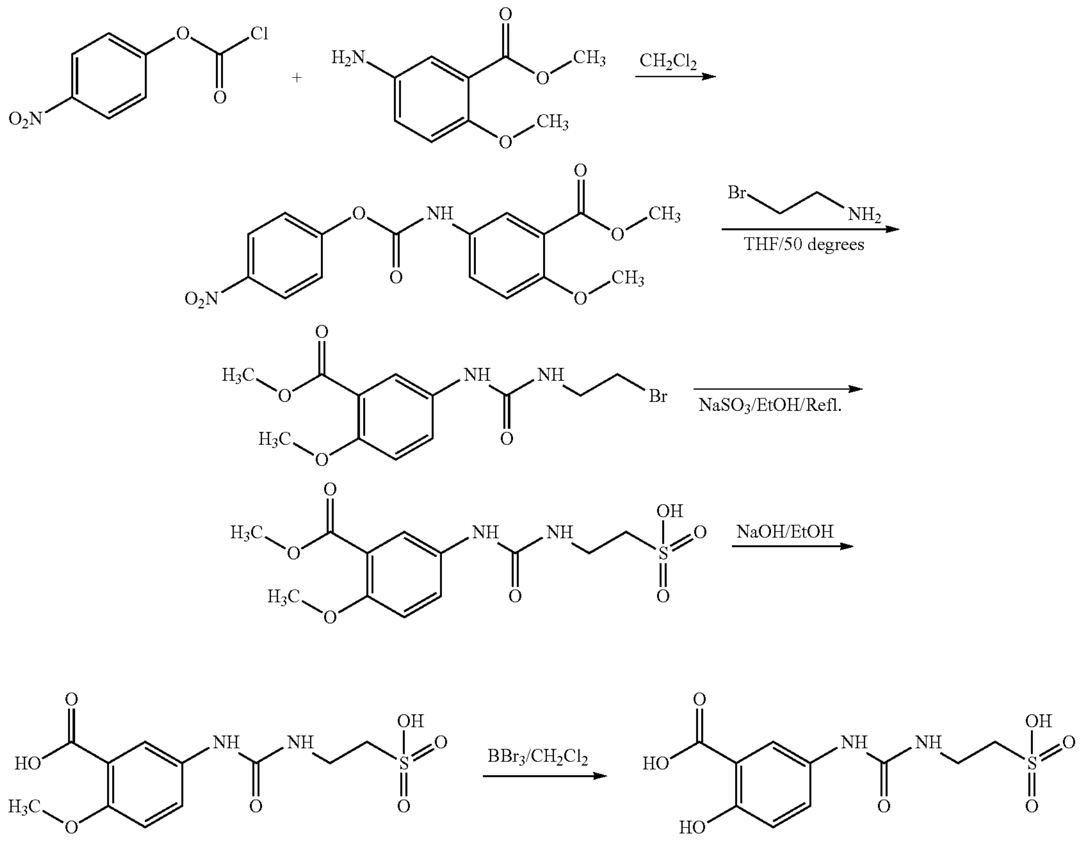
11
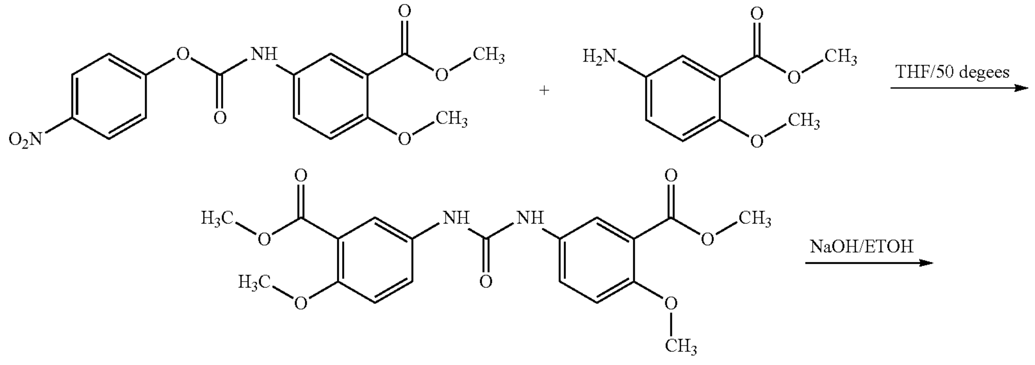

-continued

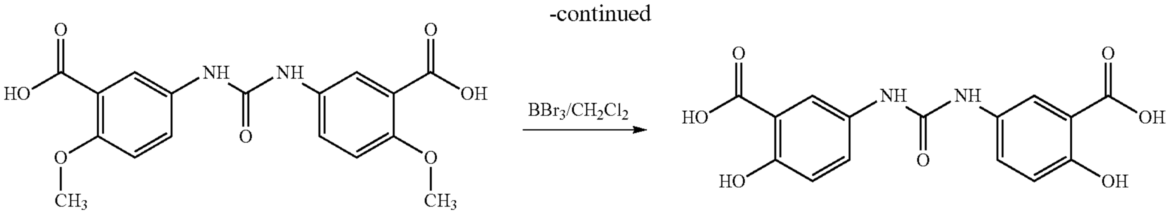

Active metabolites of compounds of the invention therefore include compounds (XVIII)-(XV):

(XIII)

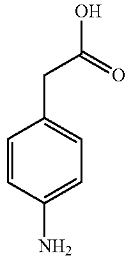

(XIV)

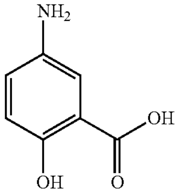

(XV)

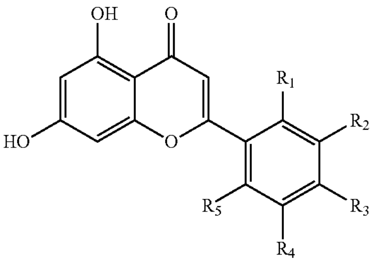

wherein each of $R^1$, $R^2$, $R^3$, $R^4$ and $R^5$ is independently selected from among H and OH.

Such active metabolites therefore may be directly administered to a subject in need thereof for treating and preventing the disease states or physiological conditions for which such active metabolites are effective, by incorporating such active metabolites in a suitable dose or delivery form, such as a capsule or tablet form for oral administration, in which the capsule or tablet is effective to deliver the active metabolites to the colon for therapeutic action at such locus.

The compounds and active metabolites of the invention are readily synthesized within the skill of the art, based on the disclosure herein.

Synthesis of compounds of the Formula (I) type can for example be carried out by illustrative reaction schemes such as the following:

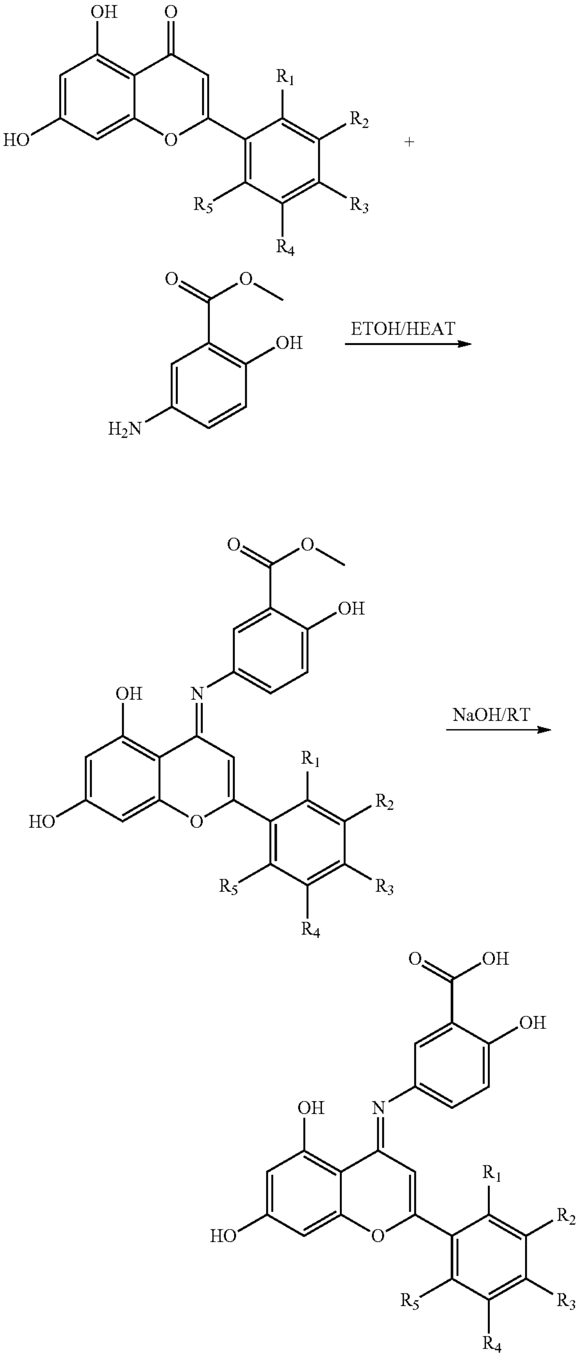

wherein each of $R^1$, $R^2$, $R^3$, $R^4$ and $R^5$ is independently selected from among H and OH.

Compounds of the Formula (II) type can be made by synthetic procedures such as the following illustrated syntheses:
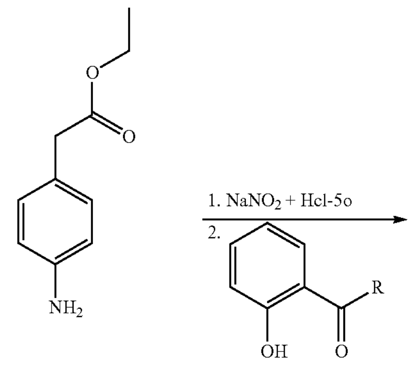
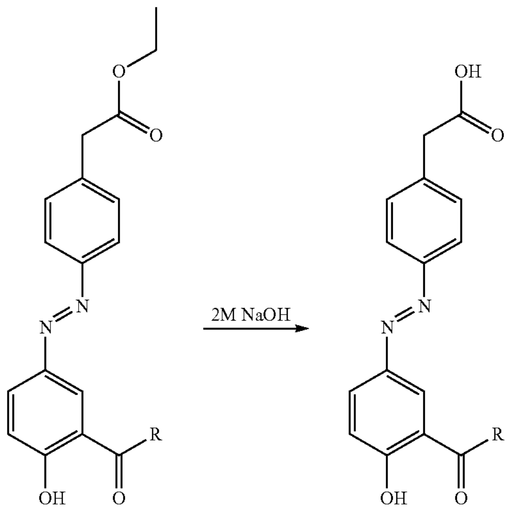
or
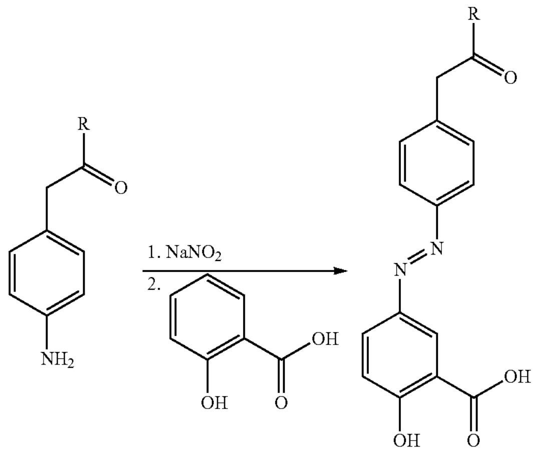
or
-continued
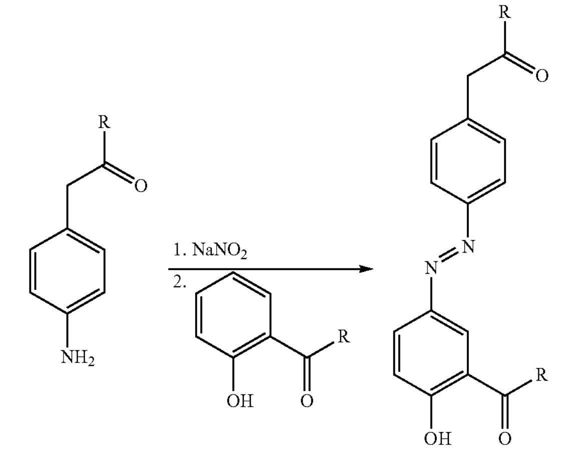
wherein each R is selected from the group consisting of —OH, —$HNCH_2CH_2SO_3H$, —$HNCH_2CH_2SO_2N_3$, —$HNCH_2CH_2SO_2NHR^6$, —$HNCH_2CO_2H$ and —HNCH$(CO_2H)CH_2COOH$;
Compounds of the Formula (III) type can be made by synthetic procedures such as the following:
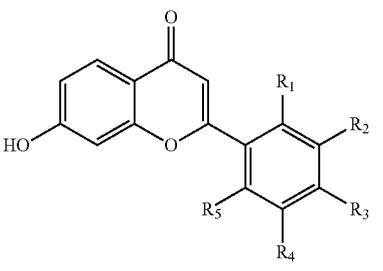
+
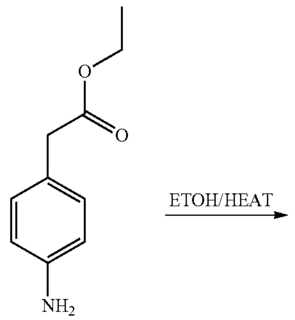

-continued

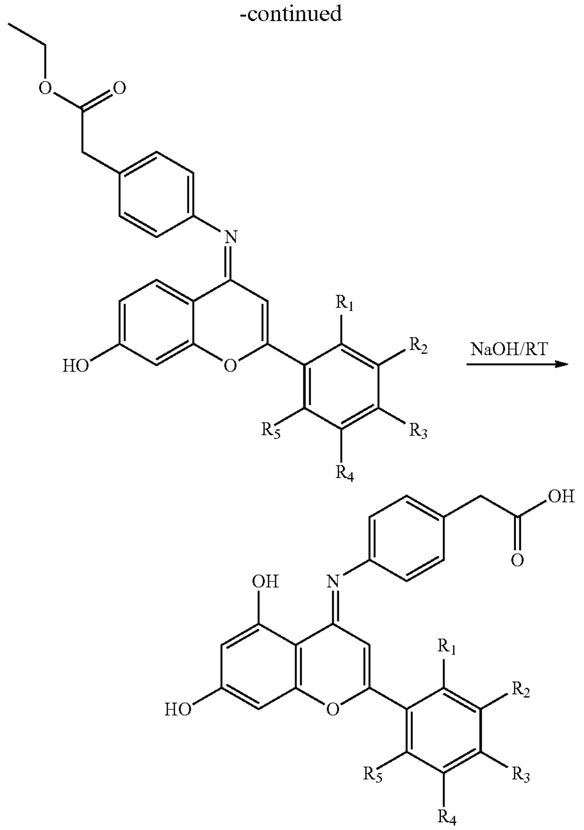

wherein each of $R^1$, $R^2$, $R^3$, $R^4$ and $R^5$ is independently selected from among H and OH.

Functionalization of the Aryl Rings on the Compounds

The structures that define the compounds described herein also include a functional group, Z, which can be H or a variety of substituents on the aryl rings. The aryl rings present in the starting materials used to prepare the compounds described herein are either commercially available, or can be prepared from commercially available starting materials. Those that are not commercially available can be made by a variety of synthetic methodologies, related to the particular moieties and the particular substitution desired. The variation in synthetic methodology will be readily apparent to those of skill in the art of organic synthesis.

Those skilled in the art will readily understand that incorporation of other substituents onto the aryl or heteroaryl rings used as a starting material to prepare the compounds described herein, or intermediates thereof, can be readily realized. Also, various substituents can be added after the various linking reactions, such as azo formation, amide formation, urea/thiourea formation, imine formation, and the like, have been completed. Such substituents can provide useful properties in and of themselves or serve as a handle for further synthetic elaboration.

Substituents typically can be added to an aryl ring before reaction with a further aryl ring, such as after formation of a diazonium salt, or to the aryl ring before or after an amidation, urea/thiourea or imine synthesis step has been conducted, as discussed above.

One proviso is that such substitution should survive the synthesis conditions, such as:

a) coupling an aryl ring with a diazonium salt to a second aryl ring, or b) the reaction of an isocyanate with an amine to form a urea or a thiol, an isothiocyanate and an amine to form a thiourea, an isocyanate and a hydroxy group to form a carbamate, or a hydroxy group and an isothiocyanate to form a thiocarbamate, or c) the reaction of a ketone and an amine to form an imine, or should be added after the coupling chemistry is complete.

For example, aryl rings can be halogenated using various known procedures, which vary depending on the particular halogen. Examples of suitable reagents include bromine/water in concentrated HBr, thionyl chloride, pyr-ICl, fluorine and Amberlyst-A. A number of other analogs, bearing substituents in a diazotized position of an aryl ring, can be synthesized from the corresponding aniline compounds, via the diazonium salt intermediate. The diazonium salt intermediates can be prepared using known chemistry, for example, treatment of aromatic amines such as aniline with sodium nitrite in the presence of a mineral acid.

Diazonium salts can be formed from anilines, which in turn can be prepared from nitrobenzenes (and analogous amine-substituted heteroaryl rings can be prepared from nitro-substituted heteroaryl rings). The nitro derivatives can be reduced to the amine compound by reaction with a nitrite salt, typically in the presence of an acid. Other substituted analogs can be produced from diazonium salt intermediates, including, but are not limited to, hydroxy, alkoxy, fluoro, chloro, iodo, cyano, and mercapto, using general techniques known to those of skill in the art. For example, hydroxy-triphenyl methane analogues can be prepared by reacting the diazonium salt intermediate with water, protecting the resulting hydroxyl group, forming the cyclopentadienyl anion, and reacting it with a suitable aldehyde or ketone Likewise, alkoxy triphenyl methane analogues can be made by reacting the diazonium salt with alcohols. The diazonium salt can also be used to synthesize cyano or halo compounds, as will be known to those skilled in the art. Mercapto substitutions can be obtained using techniques described in Hoffman et al., *J. Med. Chem.* 36: 953 (1993). The mercaptan so generated can, in turn, be converted to an alkylthio substitutuent by reaction with sodium hydride and an appropriate alkyl bromide. Subsequent oxidation would then provide a sulfone. Acylamido analogs of the aforementioned compounds can be prepared by reacting the corresponding amino compounds with an appropriate acid anhydride or acid chloride using techniques known to those skilled in the art of organic synthesis.

Hydroxy-substituted analogs can be used to prepare corresponding alkanoyloxy-substituted compounds by reaction with the appropriate acid, acid chloride, or acid anhydride. Likewise, the hydroxy compounds are precursors of both the aryloxy and heteroaryloxy via nucleophilic aromatic substitution at electron deficient aromatic rings. Such chemistry is well known to those skilled in the art of organic synthesis. Ether derivatives can also be prepared from the hydroxy compounds by alkylation with alkyl halides and a suitable base or via Mitsunobu chemistry, in which a trialkyl- or triarylphosphine and diethyl azodicarboxylate are typically used. See Hughes, *Org. React.* (*N.Y.*) 42: 335 (1992) and Hughes, *Org. Prep. Proced. Int.* 28: 127 (1996) for typical Mitsunobu conditions.

Cyano-substituted analogs can be hydrolyzed to afford the corresponding carboxamido-substituted compounds. Further hydrolysis results in formation of the corresponding carboxylic acid-substituted analogs. Reduction of the cyano-substituted analogs with lithium aluminum hydride yields the corresponding aminomethyl analogs. Acyl-substituted analogs can be prepared from corresponding carboxylic acid-substituted analogs by reaction with an appropriate alkyllithium using techniques known to those skilled in the art of organic synthesis.

Carboxylic acid-substituted analogs can be converted to the corresponding esters by reaction with an appropriate alcohol and acid catalyst. Compounds with an ester group can be reduced with sodium borohydride or lithium aluminum hydride to produce the corresponding hydroxymethyl-substituted analogs. These analogs in turn can be converted to compounds bearing an ether moiety by reaction with sodium hydride and an appropriate alkyl halide, using conventional techniques. Alternatively, the hydroxymethyl-substituted analogs can be reacted with tosyl chloride to provide the corresponding tosyloxymethyl analogs, which can be converted to the corresponding alkylaminoacyl analogs by sequential treatment with thionyl chloride and an appropriate alkylamine. Certain of these amides are known to readily undergo nucleophilic acyl substitution to produce ketones.

Hydroxy-substituted analogs can be used to prepare N-alkyl- or N-arylcarbamoyloxy-substituted compounds by reaction with N-alkyl- or N-arylisocyanates. Amino-substituted analogs can be used to prepare alkoxycarboxamido-substituted compounds and urea derivatives by reaction with alkyl chloroformate esters and N-alkyl- or N-arylisocyanates, respectively, using techniques known to those skilled in the art of organic synthesis.

Similarly, benzene rings (and pyridine, pyrimidine, pyrazine, and other heteroaryl rings) can be substituted using known chemistry, including the reactions discussed above. For example, the nitro group on nitrobenzene can be reacted with sodium nitrite to form the diazonium salt, and the diazonium salt manipulated as discussed above to form the various substituents on a benzene ring.

Enantiomeric Purification

The compounds can occur in varying degrees of enantiomeric excess, and racemic mixtures can be purified using known chiral separation techniques.

The compounds can be in a free base form or in a salt form (e.g., as pharmaceutically acceptable salts). Examples of suitable pharmaceutically acceptable salts include inorganic acid addition salts such as sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components.

III. Methods of Treatment

The compounds described herein can be used to treat or prevent various disorders, particularly colon cancer, and inflammatory conditions of the GI tract. Such disorders include, but are not limited to, inflammatory conditions of the mouth such as mucositis, infectious diseases (e.g., viral, bacterial, and fungal diseases), and Crohn's disease; inflammatory conditions of the esophogas such as esophagitis, conditions resulting from chemical injury (e.g., lye ingestion), gastroesophageal reflux disease, bile acid reflux, Barrett's esophogas, Crohn's disease, and esophageal stricture; inflammatory conditions of the stomach such as gastritis (e.g., *Helicobacter pylori*, acid-peptic disease and atrophic gastritis), peptic ulcer disease, pre-cancerous lesions of the stomach, non-ulcer dyspepsia, and Crohn's disease; inflammatory conditions of the intestine such as celiac disease, Crohn's disease, bacterial overgrowth, peptic ulcer disease, and fissures of the intestine; inflammatory conditions of the colon such as Crohn's disease, ulcerative colitis, infectious colitis (e.g., pseudomembranous colitis such as *clostridium difficile colitis, salmonella* enteritis, *shigella* infections, yersiniosis, cryptosporidiosis, microsporidial infections, and viral infections), radiation-induced colitis, colitis in the immunocompromised host (e.g., typhlitis), precancerous conditions of the colon (e.g., dysplasia, inflammatory conditions of the bowel, and colonic polyps), proctitis, inflammation associated with hemorrhoids, proctalgia fugax, and rectal fissures; liver gallbladder and/or bilary tract conditions such as cholangitis, sclerosing cholangitis, primary bilary cirrhosis, and cholecystitis; and intestinal abscess.

The compounds described herein can also be used to diagnose constituents, conditions, or disease states in biological systems or specimens, as well as for diagnostic purposes in non-physiological systems. Furthermore, the compounds can be used to treat or prevent condition(s) or disease state(s) in plant systems. By way of example, the active component of the conjugate may have insecticidal, herbicidal, fungicidal, and/or pesticidal efficacy amenable to usage in various plant systems.

In therapeutic usage, an animal subject having or latently susceptible to an intestinal condition(s) or disease state(s) and in need of treatment therefore is treated by administering to such subject an effective amount of a compound described herein that is therapeutically effective for the condition or disease state.

Subjects to be treated by the compounds described herein include both human and non-human animal (e.g., bird, dog, cat, cow, horse) subjects, and are preferably mammalian subjects, and most preferably human subjects.

IV. Mechanism of Action

While not wishing to be bound to a particular theory, it is believed that the compounds described herein function as prodrugs that are broken down by bacterial enzymes in the colon site into active compounds. This is not to say that the compounds themselves are not active, but to say that the metabolites, or at least one of the metabolites, are, themselves, active compounds. The metabolic pathways of certain of the compounds described herein are provided below.

IMMUNOMODULATING DERICATIVES OF 5-ASA
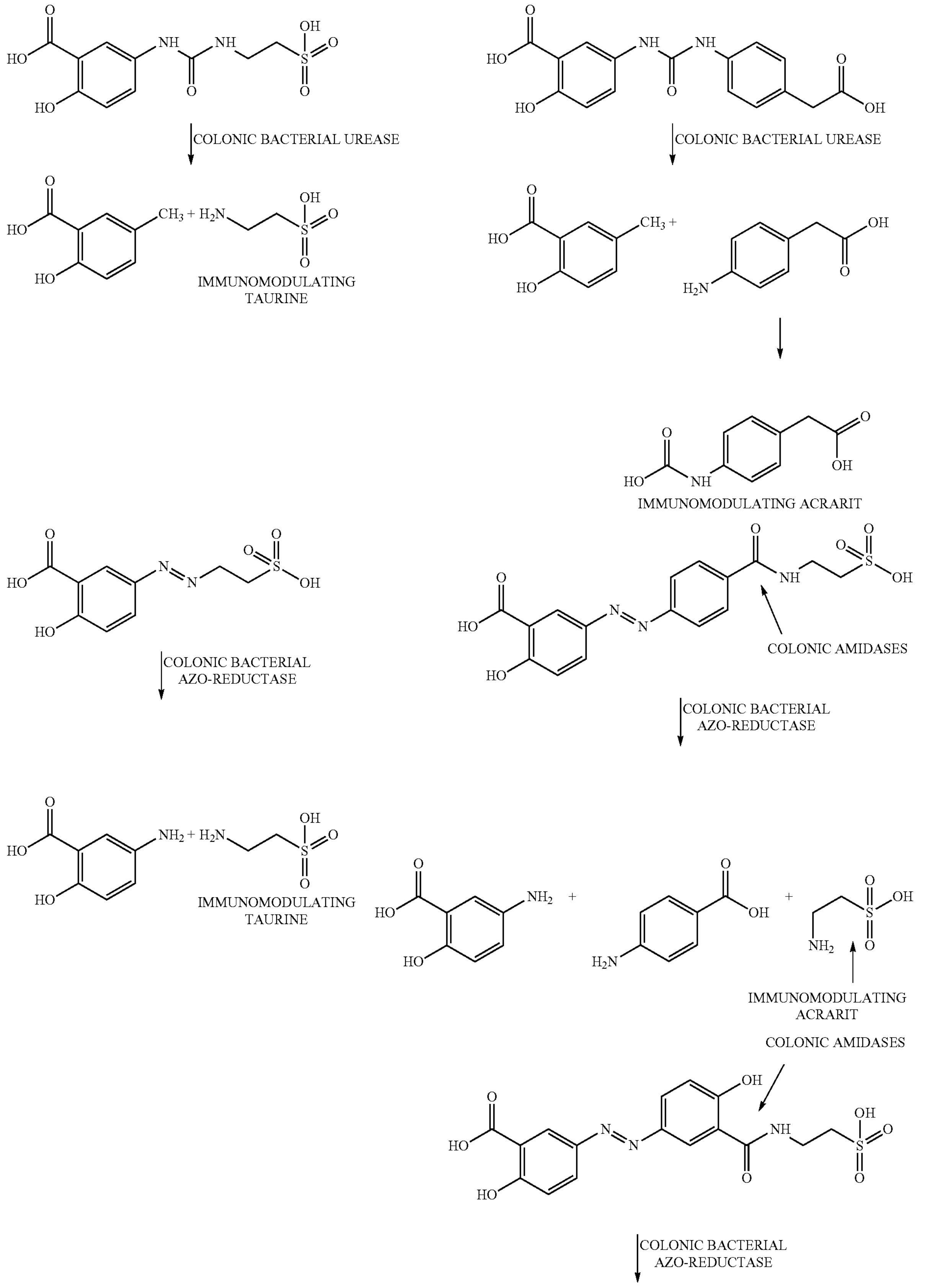

-continued

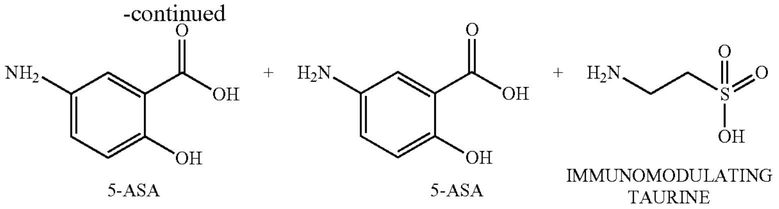

V. Pharmaceutical Compositions

Depending on the specific condition or disease state to be combated, animal subjects may be administered compounds described herein at any suitable therapeutically effective and safe dosages, as may readily be determined within the skill of the art and without undue experimentation.

The compounds described herein may be readily formulated in a variety of pharmaceutically acceptable dose forms and compositions, e.g., as described in the aforementioned U.S. Pat. No. 7,151,095, the disclosure of which is hereby incorporated herein by reference, in its entirety.

For example, the compounds described herein can be administered in specific embodiments of the invention at a dosage between about 0.1 and 200 mg/kg, preferably between about 1 and 90 mg/kg, and more preferably between about 10 and 80 mg/kg.

The compounds described herein can be administered per se as well as in the form of pharmaceutically acceptable esters, salts, and other physiologically functional derivatives thereof.

The present invention also contemplates pharmaceutical formulations, both for veterinary and for human medical use, which comprise as the active pharmaceutical ingredient one or more of the compounds described herein. In such pharmaceutical and medicament formulations, the active pharmaceutical ingredient preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and therapeutically beneficial to the recipient thereof. The active pharmaceutical ingredient is provided in an amount effective to achieve the desired pharmacological effect, as described above, and in a quantity appropriate to achieve the desired dose on a daily or other temporal basis.

The formulations include those suitable for parenteral as well as non-parenteral administration, and specific administration modalities include, but are not limited to, oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for oral and parenteral administration are preferred, with formulations suitable for oral administration most preferred.

When a compound of the present invention is utilized in a formulation comprising a liquid solution, the formulation advantageously may be administered orally or parenterally. When a compound of the present invention is employed in a liquid suspension formulation or as a powder in a biocompatible carrier formulation, the formulation may be advantageously administered orally, rectally, or bronchially.

When a compound of the present invention is utilized directly in the form of a powdered solid, the compound may advantageously be administered orally. Alternatively, it may be administered bronchially, via nebulization of the powder in a carrier gas, to form a gaseous dispersion of the powder that is inspired by the patient from a breathing circuit comprising a suitable nebulizer device.

The formulations comprising a compound of the present invention may conveniently be presented in unit dosage forms and may be prepared by any of the methods well known in the art of pharmacy. Such methods generally include the step of bringing a compound of the present invention into association with a carrier that constitutes one or more accessory ingredients. Typically, the formulations are prepared by uniformly and intimately bringing a compound of the present invention into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of a compound of the present invention as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup can be made by adding a compound of the present invention to a concentrated aqueous solution of a sugar, for example sucrose, to which may also be added any accessory ingredient(s). Such accessory ingredient(s) may include, for example, flavorings, suitable preservatives, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of a compound of the present invention, which preferably is isotonic with the blood of the recipient (e.g., physiological saline solution). Such formulations may include suspending agents and thickening agents or other microparticulate systems which are designed to target the compound to blood components or one or more organs. The formulations may be presented in unit-dose or multi-dose form.

Nasal spray formulations comprise purified aqueous solutions of a compound of the present invention with preservative agents and isotonic agents. Such formulations are preferably adjusted to a pH and isotonic state compatible with the nasal mucus membranes.

Formulations for rectal administration may be presented as a suppository with a suitable carrier such as cocoa butter, hydrogenated fats, or hydrogenated fatty carboxylic acid.

Ophthalmic formulations are prepared by a similar method to the nasal spray, except that the pH and isotonic factors are preferably adjusted to match that of the eye.

Topical formulations comprise a compound of the present invention dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

Accordingly, compounds according to the present invention may be utilized for the prophylaxis or treatment of various diseases, particularly diseases of the GI tract including, but not limited to, colon cancer, ulcerative colitis, Crohn's disease and inflammatory bowel disease.

In still other embodiments of the present invention, methods of treating or preventing colon cancer in a subject in need of such treatment or prevention include administering to the subject an effective amount of an active pharmaceutical ingredient that includes a compound of the present invention.

The active pharmaceutical compounds of the present invention can be used in therapeutic compositions which further comprise one or more other medicaments, including, by way of example, but not limited to: anti-inflammatory agents such as mesalamine, sulfasalazine, balsalazide, and olsalazine; immunomodulators such as azathioprine, 6-mercaptorpurine, cyclosporine and methotrexate; steroidal compounds such as corticosteroids; and antibiotics such as metronidazole and ciprofloxacin, as well as other ingredients such as excipients, disintegrants, release modifiers, etc.

The present invention will be better understood with reference to the following non-limiting examples.

Example 1

Development of Lead Compound, Ataza

The following example relates to the development of a lead drug candidate (referred to herein as "Ataza") that will break down in vivo to form active metabolites 5-ASA and taurine.

Inflammatory Bowel Diseases

Inflammatory bowel diseases include ulcerative colitis (UC) and Crohn's disease. Both UC and Crohn's disease are characterized by abdominal pain, bloody diarrhea, and bowel wall inflammation. Approximately 1 million Americans suffer with UC or Crohn's disease. In Western Europe and the United States the prevalence of UC is 70 to 150 per 100,000 while the prevalence of Crohn's disease is 4- to 100 per 100,000. Males and females are equally affected. Overall, the incidence of UC appears to be stabilizing, but the incidence of Crohn's disease is increasing, especially among young people.

Although the cause of inflammatory bowel disease is unknown, recent experimental and clinical studies suggest that the initiation and pathogenesis of Crohn's disease and UC are multifactorial involving interactions among genetic, environmental, and immune factors. Recently IBD has been attributed to abnormal responses to environmental triggers in genetically susceptible individuals. Available data suggest that chronic gut inflammation may result from a dysfunctional immune response to components of normal gut flora. Although no specific bacteria have been implicated in the development of IBD in humans, in genetic models of IBD in mice and rats, specific bacteria have been shown to precipitate disease. In addition, environmental factors other than microbes play a role in the pathogenesis of IBD as exemplified by the observation that smoking improves UC but worsens Crohn's disease.

There are no curative medical therapies for inflammatory bowel diseases; and even surgical resection of Crohn's disease is not a definitive cure, since the majority of patients have recurrent disease. Current treatments for inflammatory bowel disease fall into six classes: 1) corticosteroids, 2) aminosalicylates, 3) immunosuppressants, 4) antibiotics, 5) biologicals, and 6) probiotics. Although corticosteroids are effective short-term therapy long-term use is fraught with severe complications. Aminosalicylate drugs such as sulfasalazine or mesalamine (5-ASA) are the mainstay of treatment for mild and moderate disease. Immunosuppressant agents such as azathioprine and 6-mercaptpurine are used as steroid sparing agents but have a variety of adverse side effects, often precluding use in many patients. The benefit of antibiotic therapy has not been demonstrated in the overall management of this disease process but may be beneficial in patients with Crohn's disease. Antibiotics are not effective in ulcerative colitis. The importance of certain pro-inflammatory cytokines as critical mediators of gut inflammation was established by a recent series of clinical studies demonstrating that immunoneutralization of tumor necrosis factor-α (TNF-α) remarkably attenuated inflammation and tissue injury observed in Crohn's disease. Finally, probiotics have only recently come to light as potential therapies with the recognition that certain bacteria may predispose to IBD.

Ulcerative colitis responds to therapy, and has a natural history that suggests that it is a disease spectrum. What is studied as a single disease may, in fact, be a blend of several conditions whose final common denominator is diffuse inflammation of the colon associated with distortion of crypts on microscopic examination. A particular subset of ulcerative colitis patients may respond more favorable to therapy at a given stage of disease than at another stage. The host, the luminal environment, the mucosal border, and the immune system and vascular endothelium participate in the pathogenesis and healing of disease. Therapy that approaches ulcerative colitis with these distinct participants in mind may yield more success than outcomes obtained in the past two decades.

Development of ATAZA

ATAZA is a conjugate of 5-aminosalicylic acid (5-ASA) and taurine, which are chemically coupled through an azo linkage. As with balsalazide, the azo reductases produced by colonic bacteria will cleave ATAZA's azo bond, thereby releasing active moieties in the colon. The molecular weight of ATAZA is 274.28 and its structure is displayed below.

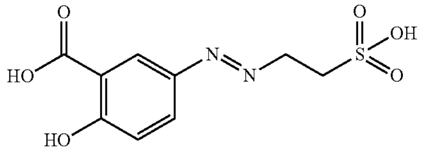 [SMILES: O=C(O)c1cc(/N=N/CCS(=O)(=O)O)ccc1O]

Rationale for Development of a Bifunctional Molecule.

Since cyclosporine was used for treatment of severe ulcerative colitis, there have been no revolutionary changes in the medial armamentarium for UC. Although the mechanism of action of 5-ASA compounds is not fully understood, it appears to be topical rather than systemic. Mucosal production of arachidonic acid metabolites, through both the cyclooxygenase, COX (i.e., prostanoids, PGE), and lipoxygenase (i.e., leukotrienes and hydroxyeicosatraenoic acids, LOX) pathways, is increased in patients with chronic inflammatory bowel disease and it is possible that 5-ASA diminishes inflammation by blocking lipoxygenase and inhibiting prostaglandin production in the colon. However, more recent evidence suggests that 5-ASA inhibits NF-kB and it is through modification of this signaling pathway, that inflammation is reduced. Other manifestations of 5-ASA's effects are reductions in expression of the cytokines IL-1, TNF-a, and IL-6 among others. Taurine is an anti-rheumatoid arthritis molecule. Interestingly, many drugs that have been shown to be effective in treating rheumatoid arthritis are also effective in treating inflammatory bowel disease. Taurine, 2-aminoethanesulfonic acid is the major intracellular free beta-amino acid. It is present in most mammalian tissues. Though not a constituent of mammalian protein, it plays many important physiological functions in osmoregulation, bile acid conjugation, modulation of the functions of the central nervous system, cell proliferation, viability and prevention of oxidant-induced injury in many tissues and as a biological antioxidant, it stabilizes biomembranes, and scavenges reactive oxygen species. It attenuates nephrotoxicity induced by tamoxifen, cisplatin in LLC-PKI renal cells; Ifosfamide induced renal dysfunction, cisplatin-induced nephrotoxicity in rats and cyclosporine A renal dysfunction in rats.

Gentamicin-induced acute tubular necrosis in rats was attenuated by taurine.

Taurine has also been shown to attenuate dextran sulfate sodium-induced colitis in mice and in combination with 5-ASA it addictively ameliorates TNBS induced colitis in rats.

Taurine has immunomodulating properties. Studies with cats deprived of taurine, (essential nutrient in their diet) showed substantial impairment in immune functions. Studies in other species have shown similar effects. Taurine interacts with hypochlorous acid, produced during "oxidative burst" of stimulated macrophages to produce taurine chloramines (Taucl). It is this form of taurine that is believed to possess most of its biological activities. Antiinflammatory effects of taurine have been documented. Taucl inhibits nuclear factor kB activation and the capacity for proinflammatory cytokine production, thus producing an anti-inflammatory effect. Taucl inhibited iNO, PGE2, TNF-alpha and IL-6 production from stimulated macrophages in cell culture. Clinically, taurine has been used with varying degrees of success in the treatment of a wide variety of conditions that include cardiovascular diseases, hypercholesterolemia, epilepsy and other seizure disorders, macular degeneration, Alzheimer's disease, hepatic disorders, alcoholism and cystic fibrosis. While not wishing to be bound to a particular theory, it is believed that taurine will suppress intestinal inflammation, ameliorate nephrotoxicity, and improve the immune system of patients to which the taurine prodrugs described herein are administered.

Toxicity

With a long history of world wide use, 5-ASA has a well-characterized safety profile with relatively few side effects, contraindications, or long-term adverse effects. Side effects of 5-ASA are generally dose dependent, mild and reversible. They include hypersensitivity reactions, gastrointestinal disturbances, dermatologic events, headache, and exacerbation of the symptoms of colitis. In addition, although the incidence of renal toxicity is rare it has been observed in animal studies and humans.

Concept

The beneficial anti-inflammatory and immunomodulatory properties of 5-ASA, and taurine, have been combined in the instant application to create "ATAZA," a prodrug form of a compound with 5-ASA and taurine as active metabolites. Following oral administration, ATAZA will be inefficiently absorbed relative to the components, 5-ASA, and taurine. However, upon reaching the colon, azo reductases produced by colonic bacterial enzymes cleave the azo bond releasing the active moieties. If given orally as separate compounds, 5-ASA, and taurine are rapidly absorbed and never achieve high concentrations in the bowel lumen (i.e., the colon site). High local concentrations of 5-ASA, and taurine delivered through ATAZA should be beneficial as local treatment of inflammatory bowel disease. It is believed that ATAZA by virtue of its anti-inflammatory and immunomodulatory effects will have benefits over and above those of conventional 5-ASA drugs that are used for inflammatory bowel disease.

Structural Formulae of APAZA and ATAZA, and Products after Azo Reductase Exposure (A) APAZA and Metabolites (B) ATAZA and Metabolites (A)

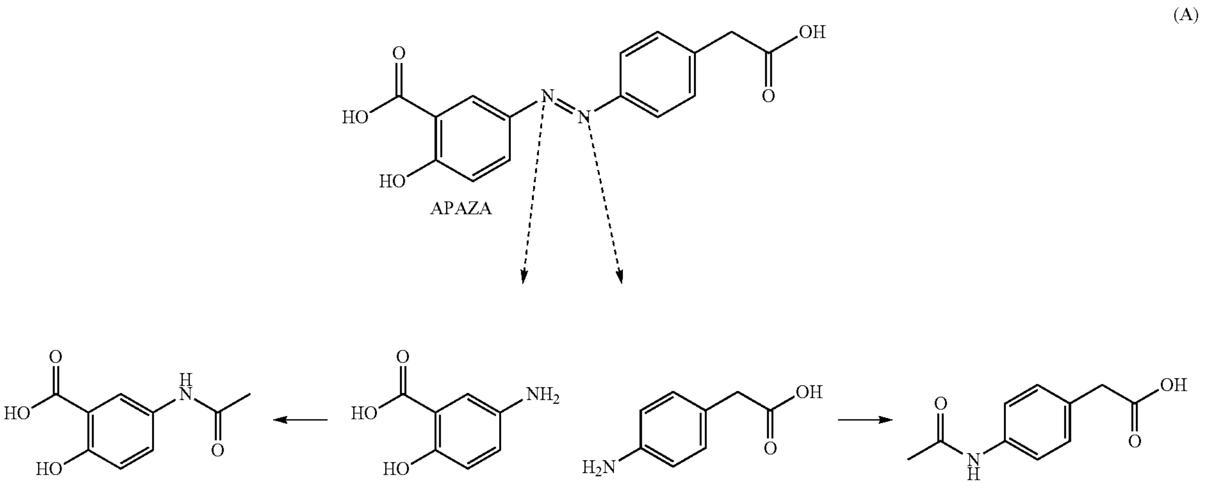

APAZA

Acetylated Metabolite

5-ASA

4-APAA

Acetylated Metabolite

*Anti-arthritis and Immunodulatory

-continued (B)

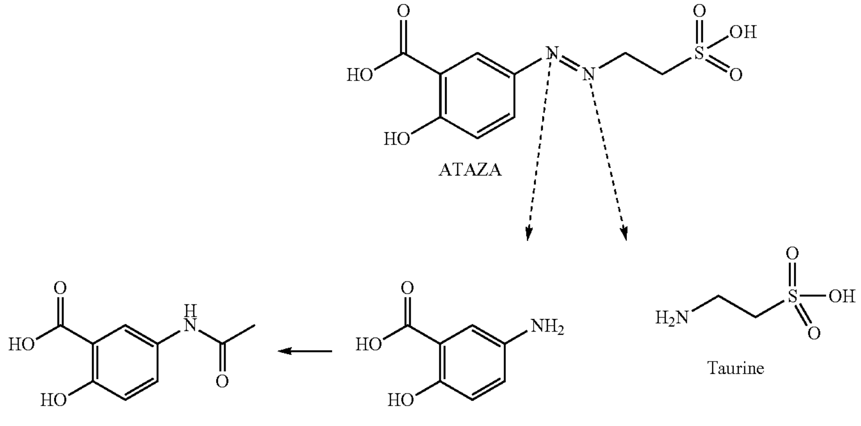

ATAZA

Acetylated Metabolite

5-ASA

Taurine

*Antiarthritis and Immunomodulatory
*Inhibits TNF-Dependment NF-kB Activities
*Inhibits COX-2 Enzyme
*Inhibits iNO Enzyme Radical Scavenger
*Antioxidant
*Stabilizes Cell Membrane

Example 2

Metabolism of Active Compounds Following Oral Delivery

The metabolism of the compounds described herein can be measured according to the protocols disclosed in U.S. Pat. No. 6,583,128. The compound to be assessed, and sulfasalazine (used as a control; not part of the present invention) can be orally dosed to rats. The degradation and the generation of their metabolites after the oral dosing can be measured to confirm that the compound undergoes bacterial azo reduction and yields its metabolites. In the case of ATAZA, for example, the metabolites are 5-aminosalicylic acid (5-ASA) and taurine.

In addition to confirming that the compounds described herein undergo a bacterial reduction process and yield their metabolites in in-vivo metabolism, the quantification of the metabolites thus formed can also be carried out. Sulfasalazine can be used as a control since the same azo bond cleavage by bacteria occurs with it, which results in 5-aminosalicylic acid and sulfapyridine as its metabolites.

A small number of rats, for example, a total of 7 rats, can be used for the experiment and methylcellulose can be used as a vehicle. The dosage amount can be 100 mg/kg per rat. Three rats can be dosed with the compound, three rats can be dosed with sulfasalazine, and one rat can be used as a control and dosed with methylcellulose. In this manner, the experiment is, in essence, run in triplicate. Both urine and feces can be collected over 2 days and analyzed by HPLC.

Urine can be collected each day, and a representative aliquot from each sample can be centrifuged for an appropriate amount of time, and an appropriate amount of supernatant injected for analysis. Feces can also be collected, for example, each day, and homogenized, for example, with a 1:1 mixture of water and acetonitrile. This mixture can then be centrifuged for an additional period of time, and an appropriate aliquot of supernatant can be injected for analysis.

A Waters 2690 HPLC can be used for sample analysis as follows:

Mobile phase programming: Gradient Mobile phase: A=Water+0.1% TFA B=Acetonitrile+0.1% TFA Flow rate: 1 mL/min. Column: Phenomenex Max RP, 80 angstroms, 4.6 mm×250 mm PDA settings: Collected spectrum: 210-400 nm Extracted chromatogram: 280 and/or other Run time/sample: Approximately 50 min.

Because the animal feces will also include other enzymes, such as ureases and amidases, other prodrug forms as described herein, such as ureas, carbamates, thioureas, thiocarbamates, amides, thioamides, and the like, can be evaluated using this approach. If metabolites other than 5-ASA will be expected to be formed, then the control should be changed to the expected metabolite, so that the expected metabolite, if actually formed, can be identified.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A compound of one of the formulas:

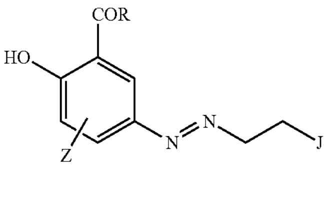

-continued

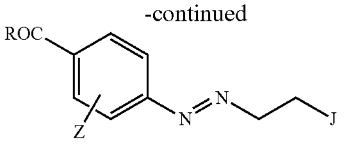

and

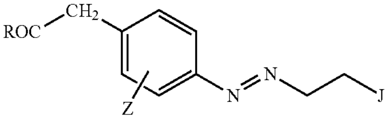

wherein:

R is selected from the group consisting of —OH, —$HNCH_2CH_2SO_3H$, —$HNCH_2CH_2SO_2N_3$, —$HNCH_2CH_2SO_2NHR^6$, —$HNCH_2CO_2H$ and —$HNCH(CO_2H)CH_2COOH$;

Z is selected from the group consisting of H, $C_{1-6}$ alkyl (including cycloalkyl), alkenyl, heterocyclyl, aryl, heteroaryl, F, Cl, Br, I, —OR', —NR'R", —$CF_3$, —CN, —$NO_2$, —$C_2R'$, —SR', —$N_3$, —C(═O)NR'R", —NR'C(═O)R", —C(═O)R', —C(═O)OR', —OC(═O)R', —OC(═O)NR'R", —NR'C(═O)O R", —$SO_2R'$, —$SO_2NR'R"$, and —$NR'SO_2R"$, R' and R" are individually hydrogen, $C_{1-6}$ alkyl, cycloalkyl, heterocyclyl, aryl, or arylalkyl;

J is selected from the group consisting of —$SO_3H$, $SO_2N_3$, $SO_2NHR^6$, and $CO_2H$; and $R^6$ is H or $C_{1-8}$ alkyl, and pharmaceutically acceptable salts and esters thereof.

2. A compound is presented by the formula:

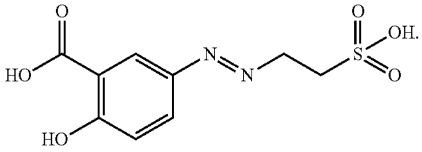 [SMILES: O=C(O)c1cc(/N=N/CCS(=O)(=O)O)ccc1O]

3. A pharmaceutical composition comprising a dose form including one of more of compounds of claim 1.

4. The composition of claim 3, further comprising a co-active ingredient selected from among anti-inflammatory agents, immunomodulators, steroidal compounds and antibiotics.

* * * * *